US010071379B2

(12) United States Patent
Fraden et al.

(10) Patent No.: US 10,071,379 B2
(45) Date of Patent: Sep. 11, 2018

(54) MANIPULATION OF FLUIDS AND REACTIONS IN MICROFLUIDIC SYSTEMS

(71) Applicant: Brandeis University, Waltham, MA (US)

(72) Inventors: Seth Fraden, Newton, MA (US); Galder Cristobal-Azkarate, Bordeaux (FR)

(73) Assignee: Brandeis University, Waltham, MA (US)

( * ) Notice: Subject to any disclaimer, the term of this patent is extended or adjusted under 35 U.S.C. 154(b) by 11 days.

(21) Appl. No.: 15/257,017

(22) Filed: Sep. 6, 2016

(65) Prior Publication Data

US 2017/0007998 A1  Jan. 12, 2017

Related U.S. Application Data

(63) Continuation of application No. 14/577,652, filed on Dec. 19, 2014, now Pat. No. 9,440,232, which is a (Continued)

(51) Int. Cl.
*G01N 1/38* (2006.01)
*B01L 3/00* (2006.01)
(Continued)

(52) U.S. Cl.
CPC ..... *B01L 3/502784* (2013.01); *B01L 3/50273* (2013.01); *B01L 3/502715* (2013.01); *B01L 3/502746* (2013.01); *C30B 7/00* (2013.01); *C30B 29/58* (2013.01); *G01N 1/38* (2013.01); *B01L 3/06* (2013.01); *B01L 3/5027* (2013.01); *B01L 7/54* (2013.01); *B01L 2200/0621* (2013.01); *B01L 2200/0642* (2013.01); *B01L 2200/0668* (2013.01); *B01L 2200/0673* (2013.01); *B01L 2300/0816* (2013.01); *B01L 2300/0864* (2013.01); *B01L 2300/0867* (2013.01); *B01L 2300/1822* (2013.01); *B01L 2400/0406* (2013.01);
(Continued)

(58) Field of Classification Search
None
See application file for complete search history.

(56) References Cited

FOREIGN PATENT DOCUMENTS

WO WO-2005021151 A1 * 3/2005 ............ B01F 5/0646

* cited by examiner

*Primary Examiner* — Paul S Hyun
(74) *Attorney, Agent, or Firm* — Brown Rudnick LLP; Thomas C. Meyers

(57) ABSTRACT

Microfluidic structures and methods for manipulating fluids and reactions are provided. Such structures and methods may involve positioning fluid samples, e.g., in the form of droplets, in a carrier fluid (e.g., an oil, which may be immiscible with the fluid sample) in predetermined regions in a microfluidic network. In some embodiments, positioning of the droplets can take place in the order in which they are introduced into the microfluidic network (e.g., sequentially) without significant physical contact between the droplets. Because of the little or no contact between the droplets, there may be little or no coalescence between the droplets. Accordingly, in some such embodiments, surfactants are not required in either the fluid sample or the carrier fluid to prevent coalescence of the droplets. Structures and methods described herein also enable droplets to be removed sequentially from the predetermined regions.

9 Claims, 18 Drawing Sheets

Related U.S. Application Data continuation of application No. 14/294,737, filed on Jun. 3, 2014, now Pat. No. 9,017,623, which is a continuation of application No. 12/525,749, filed as application No. PCT/US2008/001544 on Feb. 6, 2008, now Pat. No. 8,772,046.

(60) Provisional application No. 60/899,849, filed on Feb. 6, 2007.

(51) Int. Cl.
| | | |
|---|---|---|
| *C30B 7/00* | (2006.01) | |
| *C30B 29/58* | (2006.01) | |
| *B01L 3/06* | (2006.01) | |
| *B01L 7/00* | (2006.01) | |

(52) U.S. Cl.
CPC *B01L 2400/0655* (2013.01); *G01N 2001/386* (2013.01); *Y10T 137/0318* (2015.04); *Y10T 436/2575* (2015.01)

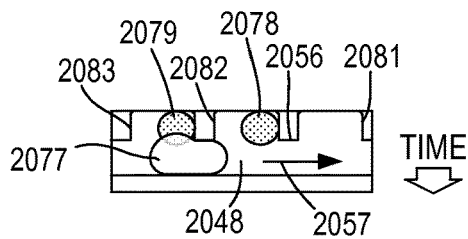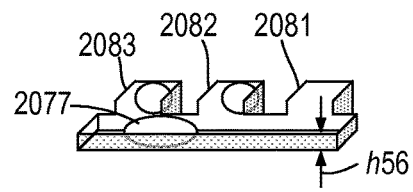
Fig.11A  Fig.11A-1
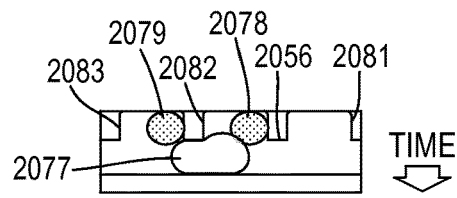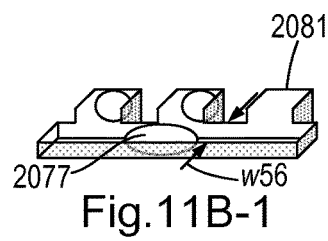
Fig.11B  Fig.11B-1
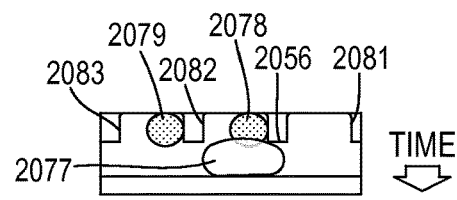
Fig.11C
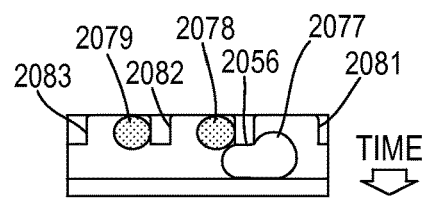
Fig.11D
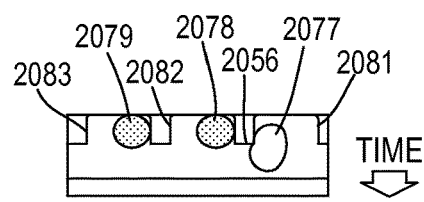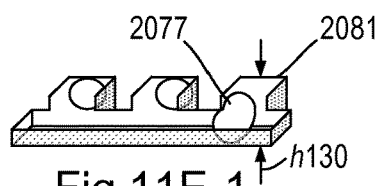
Fig.11E  Fig.11E-1
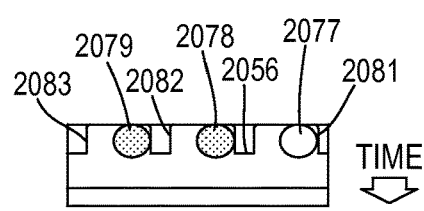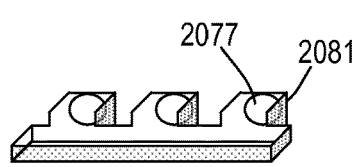
Fig.11F  Fig.11F-1

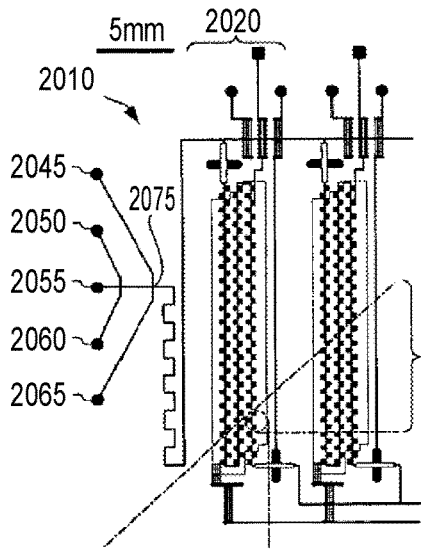
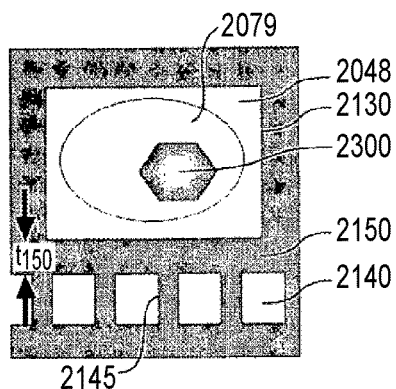
Fig. 14A
Fig. 14B
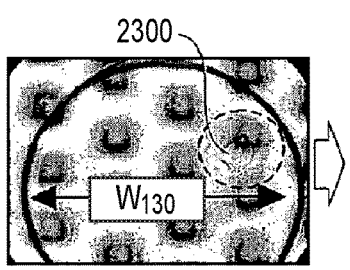
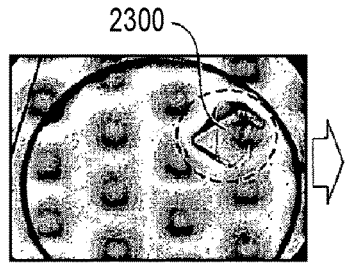
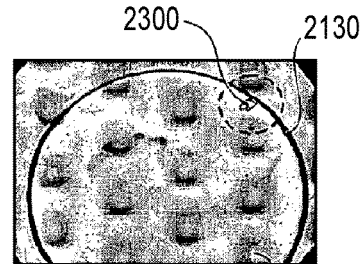
Fig. 14C
Fig. 14D
Fig. 14E
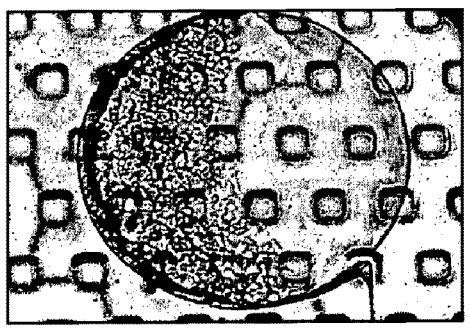
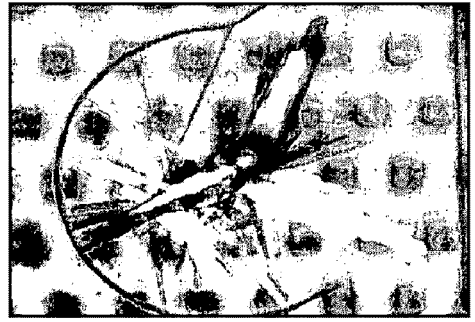
Fig. 14F
Fig. 14G

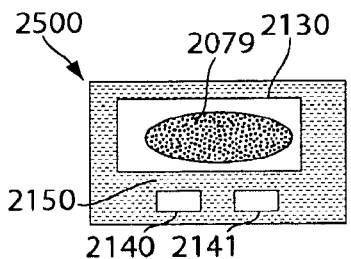
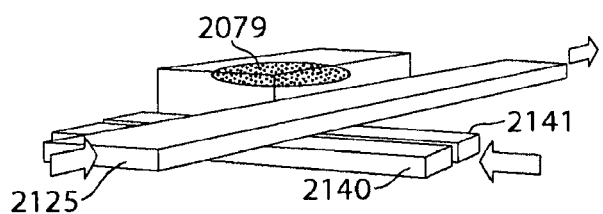
Fig. 18A      Fig. 18B
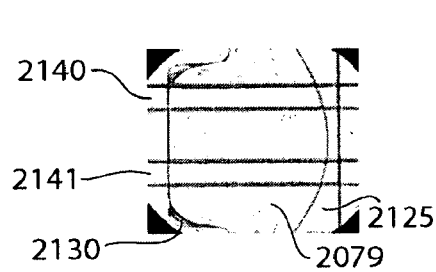
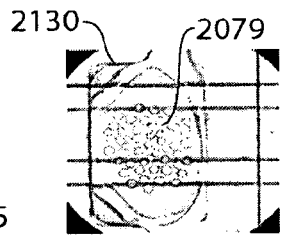
Fig. 18C      Fig. 18D
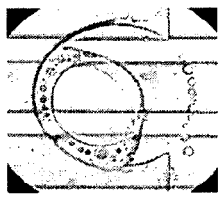
Fig. 18E      Fig. 18F
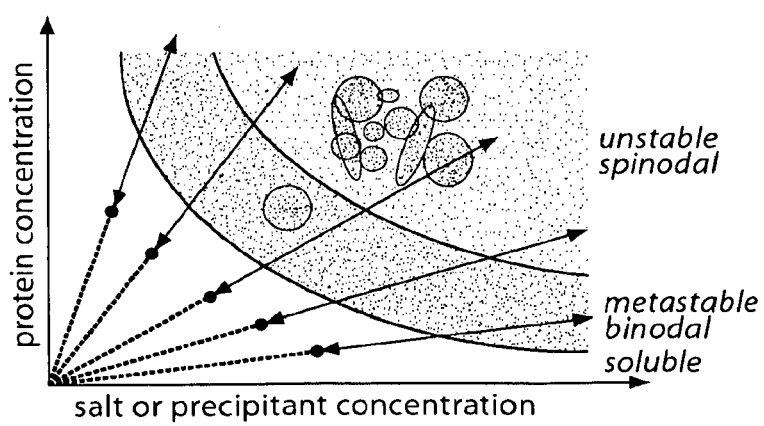
Fig. 18G

MANIPULATION OF FLUIDS AND REACTIONS IN MICROFLUIDIC SYSTEMS

RELATED APPLICATIONS

This application is a continuation of U.S. application Ser. No. 14/577,652, filed Dec. 19, 2014, which is a continuation of U.S. application Ser. No. 14/294,737, filed Jun. 3, 2014, which is a continuation of U.S. application Ser. No. 12/525,749, filed Mar. 9, 2010, which is a U.S. National Stage filing of PCT/US2008/001544, filed Feb. 6, 2008, which claims priority to U.S. Provisional Application 60/899,849, filed Feb. 6, 2007, all of which are incorporated herein by reference in their entirety.

FIELD OF INVENTION

The present invention relates generally to microfluidic structures, and more specifically, to microfluidic structures and methods including microreactors for manipulating fluids and reactions.

BACKGROUND

Microfluidic systems typically involve control of fluid flow through one or more microchannels. One class of systems includes microfluidic "chips" that include very small fluid channels and small reaction/analysis chambers. These systems can be used for analyzing very small amounts of samples and reagents and can control liquid and gas samples on a small scale. Microfluidic chips have found use in both research and production, and are currently used for applications such as genetic analysis, chemical diagnostics, drug screening, and environmental monitoring. Although these systems may allow manipulation of small volumes of fluids, additional methods that allow further control and flexibility are needed.

SUMMARY OF THE INVENTION

Microfluidic structures including microreactors for manipulating fluids and reactions and methods associated therewith are provided.

In one aspect of the invention, a method is provided. The method comprises providing a microfluidic network comprising a first region and a microfluidic channel in fluid communication with the first region, flowing a first fluid in the microfluidic channel, flowing a first droplet comprising a second fluid in the microfluidic channel, wherein the first fluid and the second fluid are immiscible, positioning the first droplet at the first region, and maintaining the first droplet at the first region while the first fluid is flowing in the microfluidic channel, wherein positioning and/or maintaining the first droplet at the first region does not require the use of a surfactant in the first or second fluids.

In some instances in connection with the methods described herein, the first and/or second fluids does not comprise a surfactant. The method may further comprise flowing a second droplet comprising a third fluid in the microfluidic channel, wherein the third fluid and the first fluid are immiscible, and positioning the second droplet at a second region in fluid communication with the microfluidic channel. In some instances, the third fluid does not comprise a surfactant. In other instances, the first and second droplets do not come into physical contact with each other during the positioning and/or maintaining steps.

In some embodiments in connection with the methods described herein, positioning and/or maintaining the first droplet at the first region is independent of flow rate of the first fluid in the microfluidic channel.

In some embodiments in connection with the methods described herein, the first region is closer in distance to a first inlet of the microfluidic network for introducing the first fluid into the microfluidic channel than the second region.

In some embodiments in connection with the methods described herein, the first droplet is positioned at the first region before the second droplet is positioned in the second region.

In some embodiments in connection with the methods described herein, the method further comprises removing the first droplet from the first region and then removing the second droplet from the second region.

In some embodiments in connection with the methods described herein, the method comprises flowing a fluid comprising a surfactant in the microfluidic channel.

In some embodiments in connection with the methods described herein, the method comprises coating the first and/or second droplets with a surfactant.

In some embodiments in connection with the methods described herein, the method comprises dewetting the first and/or second droplets from a surface of the microfluidic channel.

In some embodiments in connection with the methods described herein, the first and second droplets are removed from the first and second regions, respectively, by reversing a direction of flow in the microfluidic channel.

In some embodiments in connection with the methods described herein, positioning of the first droplet at the first region affects a direction of flow of a second droplet in the microfluidic network compared to when the first droplet is not positioned at the first region.

In some embodiments in connection with the methods described herein, the first droplet is positioned at the first region while the first fluid is flowing in the microfluidic channel.

In some embodiments in connection with the methods described herein, the microfluidic channel comprises an upstream portion, a downstream portion, and first and second fluid paths, at least one fluid path branching from the upstream portion and reconnecting at the downstream portion.

In some embodiments in connection with the methods described herein, the first and second fluid paths have different resistances to flow.

In some embodiments in connection with the methods described herein, the first region is positioned within the first fluid path. In some cases, the first fluid path has less resistance to flow compared to the second fluid path prior to positioning of a first droplet at the first region, and the first fluid path has greater resistance to flow after positioning of the first droplet at the first region.

In some embodiments in connection with the methods described herein, the method comprises positioning several droplets at regions of the microfluidic network, wherein the droplets are positioned in the regions in the order the droplets are introduced into the microfluidic network.

In some embodiments in connection with the methods described herein, the method comprises removing several droplets positioned at regions of the microfluidic network, wherein the droplets are removed in the order the droplets were introduced into the microfluidic network.

In some embodiments in connection with the methods described herein, the method comprises removing several droplets positioned at regions of the microfluidic network, wherein the droplets are removed in the reverse order the droplets were introduced into the microfluidic network.

In another aspect of the invention, a method is provided. The method comprises providing a microfluidic network comprising at least a first inlet to a microfluidic channel, a first and a second region for positioning a first and a second droplet, respectively, the first and second regions in fluid communication with the microfluidic channel, wherein the first region is closer in distance to the first inlet than the second region, flowing a first fluid in the microfluidic channel, flowing a first droplet, defined by a fluid immiscible with the first fluid, in the microfluidic channel, positioning the first droplet at the first region, flowing a second droplet, defined by a fluid immiscible with the first fluid, in the microfluidic channel past the first region without the second droplet physically contacting the first droplet, and positioning the second droplet at the second region.

In one aspect of the invention, a method is provided. The method comprises positioning a first droplet defined by a first fluid, and a first component within the first droplet, in a first region of a microfluidic network, forming a first precipitate of the first component in the first droplet while the first droplet is positioned in the first region, dissolving a portion of the first precipitate of the first compound within the first droplet while the first droplet is positioned in the first region, and re-growing the first precipitate of the first component in the first droplet.

In another aspect of the invention, a method is provided. The method comprises positioning a droplet defined by a first fluid, and a first component within the droplet, in a first region of a microfluidic network, the droplet being surrounded by a second fluid immiscible with the first fluid, positioning a third fluid in a reservoir positioned adjacent to the first region, the reservoir being separated from the region by a semi-permeable barrier, changing a concentration of the first component within the first fluid of the droplet, and allowing a concentration-dependent chemical process involving the first component to occur within the droplet.

In another aspect of the invention, a method is provided. The method comprises positioning a droplet defined by a first fluid, and a first component within the droplet, in a first region of a microfluidic network, the droplet being surrounded by a second fluid immiscible with the first fluid, flowing a third fluid in a microfluidic channel in fluid communication with the first region and causing a portion of the second fluid to be removed from the first region, changing the volume of the droplet and thereby changing a concentration of the first component within the droplet, and allowing a concentration-dependent chemical process involving the first component to occur within the droplet.

In another aspect of the invention, a device is provided. The device comprises a fluidic network comprising a first region and a first microfluidic channel allowing fluidic access to the first region, the first region constructed and arranged to allow a concentration-dependent chemical process to occur within said first region, wherein the first region and the first microfluidic channel are defined by voids within a first material, a reservoir adjacent to the first region and a second microfluidic channel allowing fluidic access to the reservoir, the reservoir defined at least in part by a second material that can be the same or different than the first material, a semi-permeable barrier positioned between the reservoir and the first region, wherein the barrier allows passage of a first set of low molecular weight species, but inhibits passage of a second set of large molecular weight species between the first region and the reservoir, the barrier not constructed and arranged to be operatively opened and closed to permit and inhibit, respectively, fluid flow in the first region or the reservoir, wherein the device is constructed and arranged to allow fluid to flow adjacent to a first side of the barrier without the need for fluid to flow through the barrier, and wherein the barrier comprises the first material, the second material, or a combination of the first and second materials.

In another aspect of the invention, a method is provided. The method comprises providing a fluidic network comprising a first region, a microfluidic channel allowing fluidic access to the first region, a reservoir adjacent to the first region, and a semipermeable barrier positioned between the first region and the reservoir, wherein the first region is constructed and arranged to allow a concentration-dependent chemical process to occur within the first region, and wherein the barrier allows passage of a first set of low molecular weight species, but inhibits passage of a second set of large molecular weight species between the first region and the reservoir, providing a droplet defined by a first fluid in the first region, providing a second fluid in the reservoir, causing a component to pass across the barrier, thereby causing a change in a concentration of the first component in the first region, and allowing a concentration-dependent chemical process involving the first component to occur within the first region.

In another aspect of the invention, a method is provided. The method comprises providing a fluidic network comprising a first region and a first microfluidic channel allowing fluidic access to the first region, the first region constructed and arranged to allow a concentration-dependent chemical process to occur within said first region, wherein the first region and the microfluidic channel are defined by voids within a first material, positioning a first fluid containing a first component in the first region, positioning a second fluid in a reservoir via a second microfluidic channel allowing fluidic access to the reservoir, the reservoir and the second microfluidic channel being defined by voids in a second material, and the reservoir being separated from the first region by a semi-permeable barrier, wherein the barrier comprises the first and/or second materials, changing a concentration of the first component in the first region, and allowing a concentration-dependent chemical process involving the first component to occur within the first region.

In another aspect of the invention, a method is provided. The method comprises positioning a first droplet defined by a first fluid, and a first component within the droplet, in a first region of a microfluidic network, positioning a second droplet defined by a second fluid, and a second component within the droplet, in a second region of the microfluidic network, wherein the first and second droplets are in fluid communication with each other, forming a first precipitate of the first component in the first droplet while the first droplet is positioned in the first region, forming a second precipitate of the second component in the second droplet while the second droplet is positioned in the second region, simultaneously dissolving a portion of the first precipitate and a portion of the second precipitate within the first and second droplets, respectively, and re-growing the first precipitate in the first droplet and re-growing the second precipitate in the second droplet, while the first and second droplets are positioned in the first and second regions, respectively.

In another aspect of the invention, a method is provided. The method comprises providing a microfluidic network comprising a first region and a microfluidic channel in fluid communication with the first region, the first region having at least one dimension larger than a dimension of the microfluidic channel, flowing a first fluid in the microfluidic channel, flowing a first droplet comprising a second fluid in the microfluidic channel, wherein the first fluid and the second fluid are immiscible, and while the first fluid is flowing in the microfluidic channel, positioning the first droplet in the first region, the first droplet having a lower surface free energy when positioned in the first region than when positioned in the microfluidic channel.

In another aspect of the invention, a method is provided. The method comprises providing a microfluidic network comprising a first region and a microfluidic channel in fluid communication with the first region, flowing a first fluid in the microfluidic channel, flowing a first droplet comprising a second fluid in the microfluidic channel, wherein the first fluid and the second fluid are immiscible, while the first fluid is flowing in the microfluidic channel, positioning the first droplet in the first region, and maintaining the first droplet in the first region while the first fluid is flowing in the microfluidic channel.

In another aspect of the invention, a method is provided. The method comprises providing a microfluidic network comprising at least a first inlet to a microfluidic channel, a first and a second region for positioning a first and a second droplet, respectively, the first and second regions in fluid communication with the microfluidic channel, wherein the first region is closer in distance to the first inlet than the second region, flowing a first fluid in the microfluidic channel, flowing a first droplet, defined by a fluid immiscible with the first fluid, in the microfluidic channel, while the first fluid is flowing in the microfluidic channel, positioning the first droplet in the first region, flowing a second droplet, defined by a fluid immiscible with the first fluid, in the microfluidic channel, while the first fluid is flowing in the microfluidic channel, positioning the second droplet in the second region, and maintaining the first droplet in the first region and the second droplet in the second region, respectively, while the first fluid is flowing in the microfluidic channel.

In another aspect of the invention, a method is provided. The method comprises providing a microfluidic network comprising at least a first inlet to a microfluidic channel, and a first and a second region for positioning a first and a second droplet, respectively, the first and second regions in fluid communication with the microfluidic channel, flowing a first fluid at a first flow rate in the microfluidic channel, flowing a first droplet, defined by a fluid immiscible with the first fluid, in the microfluidic channel, flowing a second droplet, defined by a fluid immiscible with the first fluid, in the microfluidic channel, flowing the first fluid at a second flow rate in the microfluidic channel, wherein the second flow rate is slower than the first flow rate, and while the first fluid is flowing at the second flow rate, positioning the first droplet in the first region and positioning the second droplet in the second region.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 11A, 11A-1, 11B, 11B-1, 11C, 11D, 11E, 11E-1, 11F, and 11F-1 show the positioning of droplets within micro wells of a microfluidic device, according to another embodiment of the invention.

FIGS. 14A-14G illustrate the processes of nucleation and growth of crystals inside a micro well of a device, according to another embodiment of the invention.

FIGS. 18A-18G show the use of another microfluidic device for manipulating fluids and reactions, according to another embodiment of the invention.

DETAILED DESCRIPTION

Figure 1A:
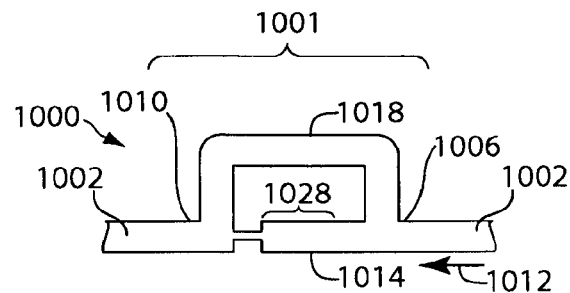
FIGS. 1A-1E show schematically a microfluidic network for positioning a droplet in a region of the network according to one embodiment of the invention.

The present invention relates to microfluidic structures and methods for manipulating fluids and reactions. Such structures and methods may involve positioning fluid samples, e.g., in the form of droplets, in a carrier fluid (e.g., an oil, which may be immiscible with the fluid sample) in predetermined regions in a microfluidic network, hi some embodiments, positioning of the droplets can take place in the order in which they are introduced into the microfluidic network (e.g., sequentially) without significant physical contact between the droplets. Because of the little or no contact between the droplets, coalescence between the droplets can be avoided. Accordingly, in such embodiments, surfactants are not required in either the fluid sample or the carrier fluid to prevent coalescence of the droplets. Positioning of droplets without the use of surfactants is desirable in certain cases where surfactants may negatively interfere with the contents in the fluid sample (e.g., proteins). Structures and methods described herein also enable droplets to be removed sequentially from the predetermined regions to a different region of the fluidic network where they can be further processed.

Once the droplets are positioned at the predetermined regions, they can be stored and/or may undergo manipulation (e.g., diffusion, evaporation, dilution, and precipitation). In some instances, many (e.g., 1000) droplets can be manipulated, sometimes simultaneously. Manipulation of fluid samples can be useful for a variety of applications, including testing for reaction conditions, e.g., in crystallization, and chemical and/or biological assays.

Microfluidic chips described herein may include a microfluidic network having a region for forming droplets of sample in a carrier fluid (e.g., an oil), and one or more microreactor regions (e.g., microwells, reservoirs, or portions of a microfluidic channel) in which the droplets can be positioned and reaction conditions within the droplet can be varied. Droplets may be positioned sequentially in regions of the microfluidic network so that upon manipulating and/or performing a chemical and/or biological process within each the droplets, the droplets can be identified at a later time, for example, to determine the particular conditions within the droplets that lead to a favorable outcome (e.g., optimal conditions for forming a product, for crystal growth, etc.).

FIG. 1 shows a method for positioning a droplet in a region of a microfluidic network according to one embodiment of the invention. As shown in illustrative embodiment of FIG. 1A, microfluidic network 1000 comprises section 1001 including microfluidic channel 1002 having an upstream portion 1006, a downstream portion 1010 (as fluid flows in the direction of arrow 1012), and fluid paths 1014 and 1018. Fluid paths 1014 and 1018 are connected, with fluid path 1018 branching off from the upstream portion and reconnecting at the downstream portion. Fluid paths 1014 and 1018 may serve as alternative paths for fluid flow. In some cases, resistance to fluid flow may differ between fluid paths 1014 and 1018. For example, fluid path 1014 may have less resistance to fluid flowing in the direction of arrow 1012 prior to positioning of a droplet in this section of the microfluidic network. As shown in this illustrative embodiment, fluid path 1014 has a lower resistance to fluid flow than fluid path 1018 due to the relatively longer channel length of fluid path 1018. It should be understood, however, that the microfluidic network may have other designs and/or configurations for imparting different relative resistances to fluid flow, and such designs and configurations can be determined by those of ordinary skill in the art. For instance, in some embodiments, the length, width, height, and/or shape of the fluid path can be designed to cause one fluid path to have a resistance to fluid flow different from another fluid path. In other embodiments, at least a portion of a fluid path may include an obstruction such as a valve (which may change resistance dynamically), a semi-permeable plug (e.g., a hydrogel), a membrane, or another structure that can impart and/or change resistance to fluid flow through that portion.

Figure 1B:
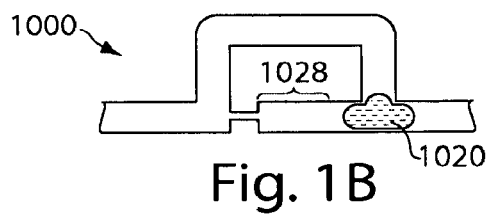
Figure 1C:
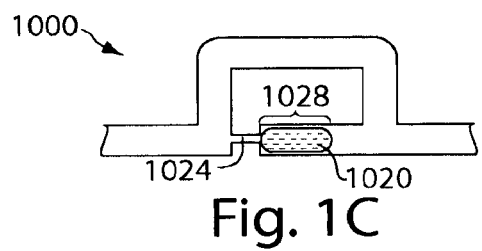

As shown in FIGS. 1B and 1C, droplet 1020 flows in the direction of 1012, e.g., by being carried by a carrier fluid flowing in the same direction. Upon passing the junction between flow paths 1014 and 1018 at upstream portion 1006, the droplet flows in fluid path 1014 due to its lower resistance to flow in that fluid path relative to fluid path 1018. However, as fluid path 1014 includes a fluid constriction, e.g., in the form of a narrow fluid path portion 1024, droplet 1020 cannot flow further down the microfluidic network. Accordingly, droplet 1020 is positioned within a region 1028 (e.g., a "micro well") of the microfluidic network. In some embodiments, droplet 1020 can be maintained at the region even though carrier fluid continues to flow in the microfluidic network (e.g., in the direction of arrow 1012).

Although FIG. 1 shows region 1028 having a cross-sectional area approximately the same as the cross-sectional area of microfluidic channel 1002, it should be understood that region 1028 can have any suitable cross-sectional area, dimensions, shape, etc. which may be suitable for containing, holding, and/or positioning a droplet.

Figure 1D:
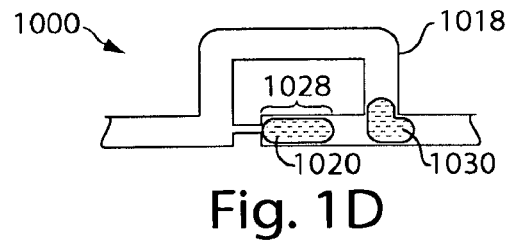
Figure 1E:
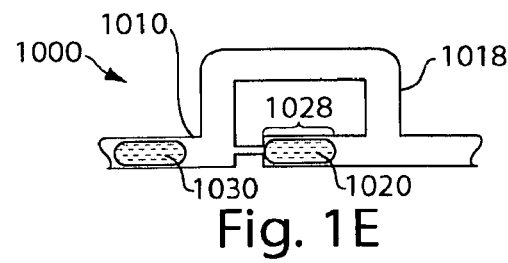

As shown in the embodiment illustrated in FIG. 1D, the positioning of droplet 1020 at region 1028 causes fluid path 1014 to be plugged such that no or minimal fluid flows past narrow fluid path portion 1024. This plugging of fluid path 1014 causes a higher resistance to fluid flow in that path compared to that of fluid path 1018. As a result, when a second droplet 1030 flows in the direction of arrow 1012, the second droplet bypasses flow path 1014 and enters flow path 1018, which now has a lower resistance than that of fluid path 1014 (FIG. 1D). Accordingly, second droplet 1030 can bypass first droplet 1020 and can now be positioned in a second region within microfluidic network 1000.

It should be understood that when droplet 1020 is positioned at region 1028, the droplet may plug all or a portion of fluid path 1014 and/or narrow fluid path portion 1024. For instance, in some cases, the droplet plugs all of such fluid paths such that none of the fluid flowing in microfluidic channel 1002 passes through narrow fluid path portion 1024. In other embodiments, the droplet may plug only a portion of such fluid paths such that some fluid passes through narrow fluid path portion 1024 even though the droplet is positioned at region 1028. The amount of fluid flowing past the droplet may depend on factors such as the dimensions of fluid path portions 1014 and/or 1024, the size of the droplets, the flow rate, etc. As long as the droplet causes fluid path 1014 to have a higher relative resistance to fluid flow than fluid path 1018, a second droplet can bypass fluid path 1014 and enter fluid path 1018.

As described above, fluid paths 1014 and 1018 may have different resistances fluid flow depending on whether or not a droplet is positioned at region 1028. In the absence of a droplet positioned at region 1028, fluid path 1014 may be configured to have a lower resistance to fluid flow than fluid path 1018. For example, greater than 50%, greater than 60%, greater than 70%, greater than 80%, or greater than 90% of the fluid flowing in channel 1002 at upstream portion 1006 may flow in fluid path 1014 compared to fluid path 1018. However, when the droplet is positioned and maintained in region 1028, fluid path 1014 may be relatively more restrictive to fluid flow. For example, less than 50%, less than 40%, less than 30%, less than 20%, or less than 10% of the fluid flowing in channel 1002 at upstream portion 1006 may flow in fluid path 1014 compared to that of 1018. In some cases, 100% of the fluid flowing in direction 1012 in microfluidic channel 1002 flows in fluid path 1018 upon positioning of a droplet in region 1028.

As illustrated in the exemplary embodiment of FIG. 1, the positioning of droplet 1020 (e.g., a first droplet) and the subsequent bypass of droplet 1030 (e.g., a second droplet) does not require contact between the first and second droplets. In certain embodiments, the second droplet does not physically contact the first droplet after positioning of the first droplet in region 1028. In other embodiments, the second droplet can come into physical contact with the first droplet as it bypasses the first droplet, however, due to such minimal contact between the two droplets, the droplets do not coalesce. Accordingly, the positioning of the droplets in the microfluidic network can take place without the use of surfactants. In other words, surfactants in either a fluid flowing in channel 1002 (e.g., a carrier fluid) or within the droplets is not required in order to stabilize the droplets and/or prevent the droplets from coalescing with one another during positioning or carrying the droplet in the microfluidic channel, and/or during maintaining the droplets within a predetermined region within the microfluidic network. However, in instances where coalescence is desired (e.g., to allow a reaction between reagents contained in two droplets), the microfluidic network and methods for operating the network can be configured to allow such physical contact and/or coalescence between droplets.

In some embodiments, methods for positioning a droplet in a microfluidic network include the steps of providing a microfluidic network comprising a first region (e.g., region 1028 of FIG. 1A) and a microfluidic channel in fluid communication with the first region, flowing a first fluid (e.g., a carrier fluid) in the microfluidic channel, and flowing a first droplet comprising a second fluid (e.g., a fluid sample) in the microfluidic channel, wherein the first fluid and the second fluid are immiscible. The first droplet may be positioned in the first region and maintained in the first region while the first fluid is flowing in the microfluidic channel. In such embodiments, positioning and/or maintaining the first droplet in the first region does not require the use of a surfactant in the first or second fluids.

In some embodiments, a chemical and/or biological process can be carried out in droplet 1020 of FIG. 1 while the droplet is positioned in region 1028. Additionally or alternatively, the droplet may be manipulated. For example, a fluid sample in the droplet may undergo a process such as diffusion, evaporation, dilution, and/or precipitation. Such methods of manipulation are described in more detail below. The droplet may be manipulation by, for example, changing the concentration of the fluid flowing in channel 1002 after the droplet has been positioned at region 1028. In other embodiments, region 1028 is in fluid communication with another fluidic channel, flow path, reservoir, or other structure, e.g., via a semi permeable membrane that may be positioned adjacent the region (e.g., underneath or above region 1028), and manipulation of the droplet can occur via such passages.

Figure 2A:
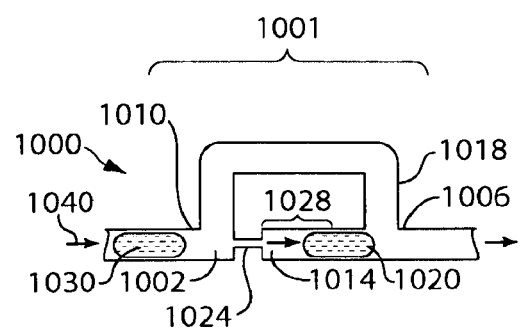
FIGS. 2A-2C show schematically removal of a droplet from a region of the network according to another embodiment of the invention.
Figure 2B:
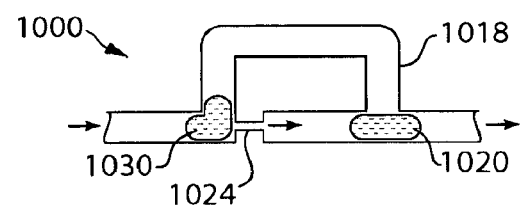
Figure 2C:
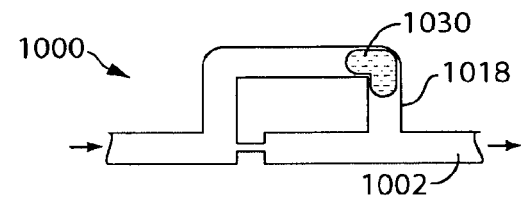

In some embodiments of the invention, droplets that have been positioned at regions of a microfluidic network can be removed or extracted from the regions to a different location in the fluidic network, where they can be optionally processed, manipulated, and/or collected. As shown in the illustrative embodiments of FIGS. 2A-2C, removing droplet 1020 from region 1028 of section 1001 of microfluidic network 1000 can take place by reversing the flow of the carrier fluid in the network such that the carrier fluid now flows in the direction of arrow 1040 (instead of in the direction of arrow 1012 of FIGS. 1A-1E).

In such embodiments, upstream portion 1006 and downstream portion 1010 of FIGS. 1A-1E now become reversed such that portion 1010 is now an upstream portion and portion 1006 is now a downstream portion. The flow of a carrier fluid in the direction of arrow 1040 in microfluidic channel 1002 causes a portion of the fluid to flow through narrow fluid path portion 1024 into region 1028 where droplet 1020 is positioned. This fluid flow causes the droplet to flow in the direction of arrow 1040. As shown in the embodiment illustrated in FIG. 2B, droplet 1030, which may have been positioned at a different region of the microfluidic network, can be removed from that region and may also flow in the direction of arrow 1040. As droplet 1030 encounters narrow fluid path portion 1024, the droplet cannot flow through this narrow opening due to its high resistance to flow. As a result, the droplet bypasses the narrow fluid path portion and flows into fluid path 1018 until it reaches microfluidic channel 1002 at downstream portion 1006. Thus, by reversing the flow and the pressure gradient in the microfluidic network, droplets 1020 and 1030 can be removed sequentially from the regions of the microfluidic network where they previously resided. That is, droplet 1020, which was positioned first before droplet 1030, can be removed from its region and can enter a different region of the microfluidic network before that of droplet 1020.

In some embodiments, sequential positioning of droplets can be performed such that a first droplet is positioned in a first region before a second droplet is positioned in a second region (and, optionally, before third, fourth, fifth droplets, etc. are positioned in their respective regions). As described above, sequential removal of the droplets can be performed such that the first droplet is removed from a region and/or positioned at a different location on the microfluidic network before the second droplet (and, optionally, before third, fourth, fifth droplets, etc. are removed from their respective regions). In other embodiments, removal of the droplets can be performed such that the second droplet is removed and/or positioned at a different location on the microfluidic network before the first droplet.

In some cases, several (e.g., greater than 2, greater than 5, greater than 10, greater than 50, greater than 100, greater than 200, greater than 500, or greater than 1000) droplets can be positioned at regions of the microfluidic network, wherein the droplets are positioned in the regions in the order the droplets are introduced into the microfluidic network. In some cases, removing several droplets positioned at regions of the microfluidic network comprises removing the droplets in the order the droplets were introduced into the microfluidic network (or in the order the droplets were positioned into the regions of the microfluidic network). In other cases, removing several droplets positioned at regions of the microfluidic network comprises removing the droplets in the reverse order the droplets were introduced into the microfluidic network (or in the reverse order the droplets were positioned into the regions of the microfluidic network). Other methods of positioning and removal of droplets are also possible.

The sequential (or predetermined/known order of) removal of droplets from regions of a microfluidic network can allow control over the identification and location of each droplet within the network. This can also allow determination of the contents inside each of the droplets from the time they are formed and/or introduced into the microfluidic network, to the time the droplets are manipulated and/or extracted from the microfluidic network.

Figure 3:
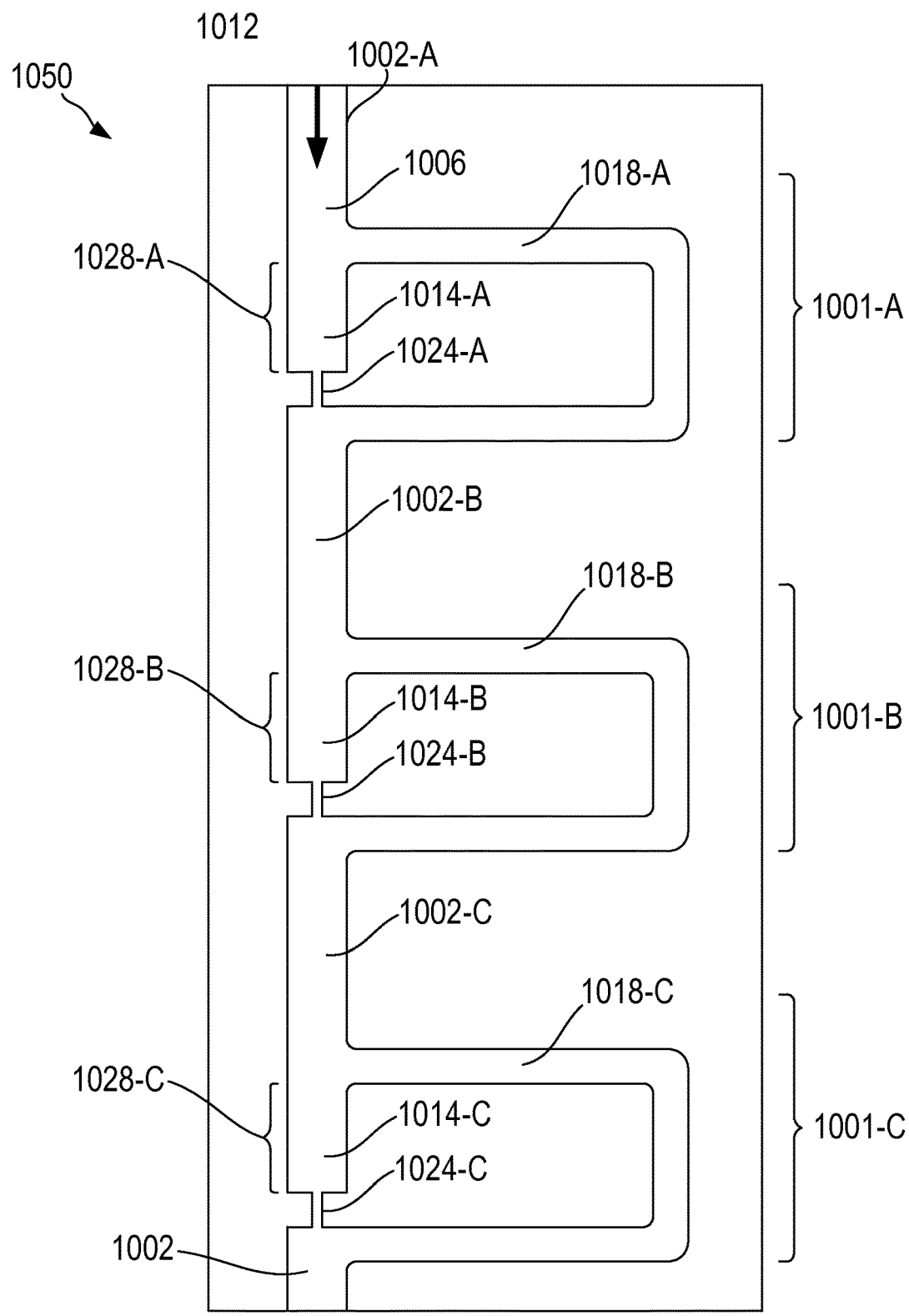
FIG. 3 is a photograph showing multiple sections of a microfluidic network for positioning droplets according to another embodiment of the invention.

FIG. 3 is a photograph of multiple sections 1001-A, 1001-B, and 1001-C of microfluidic network 1050 according to one embodiment of the invention. A carrier fluid may flow in microfluidic channel 1002-A in the direction of arrow 1012 from an inlet positioned upstream from portion 1006. The carrier fluid may partition at the junction where fluid paths 1014-A and 1018-A branch off from microfluidic channel 1002. The proportion of fluid that flows in each of the fluid paths can be determined at least in part by the relative resistance to fluid flow in the paths, as described above. In the embodiment shown in FIG. 3, sections 1001-A, 1001-B, and 1001-C are positioned in series. In other embodiments, however, such sections may be positioned in parallel and/or in both series and parallel. Other configurations are also possible.

A microfluidic network may have any suitable number of microfluidic sections 1001. For instance, the microfluidic network may have greater than or equal to 5, greater than or equal to 10, greater than or equal to 30, greater than or equal to 70, greater than or equal to 100, greater than or equal to 200, greater than or equal to 500, or greater than or equal to 1000 such sections.

In addition, although certain embodiments herein show that sections 1001 can allow positioning of a single droplet in each of the sections, in other embodiments, the sections can be designed such that greater than one droplet (e.g., greater than or equal to 2, greater than or equal to 5, or greater than or equal to 10 droplets) can be positioned at each section.

Furthermore, although only two fluid flow paths 1014 and 1018 are shown branching off from channel 1002, in other embodiments, more than two (e.g., greater than or equal to 3, greater than or equal to 5, or greater than or equal to 10) fluid paths may branch off from channel 1002. Each branching fluid path may optionally comprise one or more regions (e.g., microwells) for positioning and/or maintaining droplets.

Figure 4:
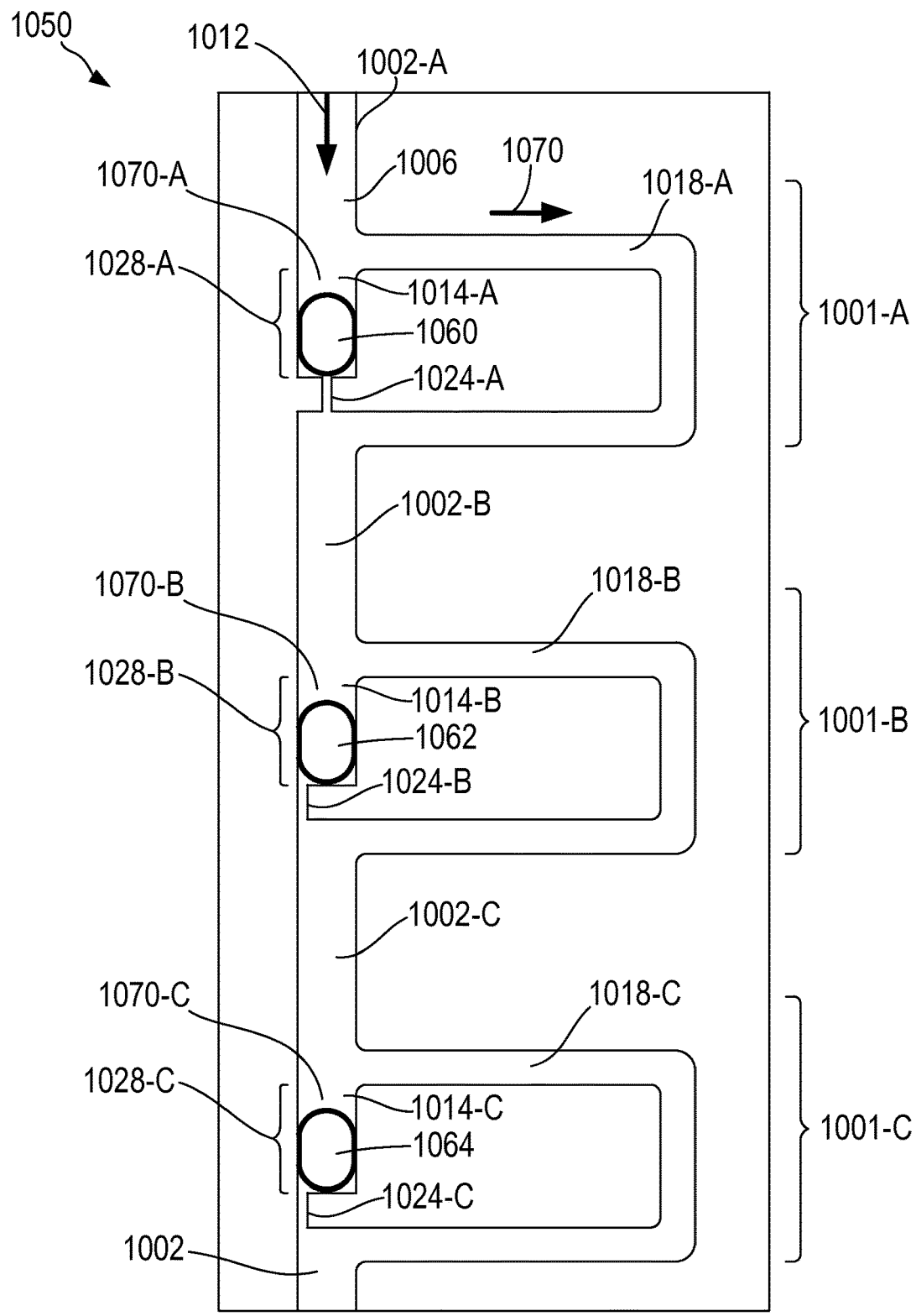
FIG. 4 is a photograph showing multiple droplets positioned in multiple regions of a microfluidic network according to another embodiment of the invention.

FIG. 4 shows the positioning of droplets 1060, 1062, and 1064 at positions 1028-A, 1028-B, and 1028-C, respectively, in micro fluidic network 1050 according to one embodiment of the invention. As shown in this illustrative embodiment, carrier fluid flows in the direction of arrow 1012 and carries droplet 1060 through channel 1002-A and into fluidic path 1014-A due to the lower resistance to fluid flow in that fluid path compared to that of fluid path 1018-A. That is, prior to the positioning of droplet 1060 in region 1028-A, more than 50% of the fluid flowing in microfluidic channel 1002-A flows through fluid path 1014-A compared to fluid path 1018-A.

Once droplet 1060 is positioned at region 1028-A, it impedes fluid flow through narrow fluid path portion 1024-A such that the resistance to fluid flow in fluid paths 1014-A and 1018-A are altered. This causes resistance to fluid flow to be higher in portion 1014-A and as a result, a greater amount of fluid flows in the direction of 1070 through fluid path portion 1018-A. Accordingly, a second droplet 1062 flowing through microfluidic channel 1002-A and passing upstream portion 1006 now bypasses fluid path portion 1014-A and flows through portion 1018-A. The second droplet, after bypassing region 1028-A, now enters microfluidic channel portion 1002-B. If there is a lower resistance to fluid flow in fluid path portion 1014-B (e.g., a droplet has not already been positioned in region 1028-B), the droplet can be positioned at this region. Next, a third droplet 1064 can flow through microfluidic channel portion 1002-A in the direction of arrow 1012 and first bypasses region 1028-A due to droplet 1060 already positioned at that region. The droplet can then flow into fluid path portion 1018-A and 1002-B. Since droplet 1062 has already been positioned at region 1028-B, third droplet 1064 bypasses this region and takes the fluid path of least resistance (fluid path portion 1018-B). Upon entering an empty region such as 1028-C, the third droplet can now position itself at that region due to a lower resistance to fluid flow in fluid path 1014-C compared to that of fluid path portion 1018-C (e.g., prior to any other droplet being positioned at region 1028-C).

Accordingly, a method for positioning droplets in regions of a microfluidic network may include providing a microfluidic network comprising at least a first inlet to a microfluidic channel (e.g., positioned upstream of portion 1006 of FIG. 4), a first region (e.g., region 1028-A) and a second region (e.g., region 1028-B) for positioning a first and a second droplet, respectively, the first and second regions in fluid communication with the microfluidic channel, wherein the first region is closer in distance to the first inlet than the second region. The method can include flowing a first fluid (e.g., a carrier fluid) in the microfluidic channel, flowing a first droplet (e.g., a first fluid sample), defined by a fluid immiscible with the first fluid, in the microfluidic channel, and positioning the first droplet in the first region. The method can also include flowing a second droplet (e.g., a second fluid sample), defined by a fluid immiscible with the first fluid, in the microfluidic channel past the first region without the second droplet physically contacting the first droplet. The second droplet may be positioned at the second region. In some instances, the first and/or second droplets are maintained at their respective regions while fluid continues to flow in the microfluidic channel.

It should be understood that other components may be integrated with fluidic networks described herein in some embodiments of the invention. For example, in some instances, resistances to fluid flow can be changed dynamically such that the direction of fluid flow (and, therefore, positioning of droplets) can be controlled by the user. In one such embodiment, valves may be positioned at one or more of positions 1070-A, 1070-B, and 1070-C of FIG. 4. For example, a valve at position 1070-B can cause restriction of fluid flow through fluid path portion 1014-B, e.g., prior to a droplet being positioned at region 1028-B. This can cause a droplet flowing through microfluidic channel portion 1002-B to bypass region 1028-B even though a droplet is not positioned at that region. Thus, the droplet flowing through portion 1002-B will flow through fluid path 1018-B and onto the next available region, where the fluid resistance of that region may or may not be controlled by a similar valve. In some instances, after a droplet bypasses region 1028-B due to a closed valve at position 1070-B (or any other component that can change the relative resistances to fluid flow between fluid paths 1014-B and 1018-B), the valve at position 1070-B can now be reopened to change the relative resistances to fluid flow such that a next droplet can now enter into region 1028-B and be positioned at that region. Such a system can allow droplets to be positioned at any desired region of a microfluidic network.

As described herein, in some embodiments droplets do not require stabilization (e.g., the use of surfactants or other stabilizing agents) in order to be positioned at predetermined regions within microfluidic networks described herein. This is because in some embodiments, the droplets do not significantly physically contact one another during bypass of one droplet to another. Due to the little or no physical contact between the droplets, the droplets do not have a chance to coalesce with one another. Thus, surfactants or other stabilizing agents are not required to stabilize the droplets from coalescence in such embodiments. In some embodiments, the absence of surfactants or other stabilizing agents causes the droplets to wet a surface of the microfluidic network. Even though wetting may occur, the droplets can still be positioned at predetermined regions within the microfluidic network due to, for example, a positive pressure that causes fluid flow to carry these droplets into these regions. As discussed above, the use of droplets and/or a carrier fluid that does not contain a surfactant is advantageous in some embodiments where surfactants may negatively interfere with contents inside the droplets. For example, the droplets may contain proteins, and surfactants are known to denature certain proteins to some extent. However, after manipulation of the droplet and/or carrying out a process such as a chemical and/or biological reaction inside the droplet, surfactants may no longer negatively affect the contents inside the droplet. Accordingly, in such cases, a surfactant or other stabilizing agent can be applied to the droplets. In some embodiments, such application of a stabilizing agent to a droplet after manipulation of the droplet and/or carrying out a process inside the droplet can facilitate mobilization of the droplet out of the region in which the droplet is positioned.

It should be understood, however, than in some embodiments, a droplet and/or a carrier fluid may contain a surfactant or other stabilizing agent that stabilizes a droplet prior to positioning of the droplet at a region in the microfluidic network. In such embodiments, the stabilization may not negatively interfere with contents (e.g., reagents) inside the droplet. Of course, such embodiments will depend on a variety of factors such as the type of stabilizing agent used, the contents inside the droplet, the application, etc.

Figure 5A:
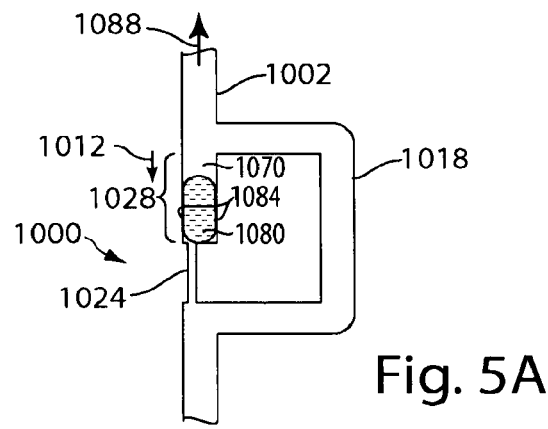
FIGS. 5A-5C show manipulation of a droplet positioned in a region of a microfluidic network by changing the surface tension of the droplet according to another embodiment of the invention.
Figure 5B:
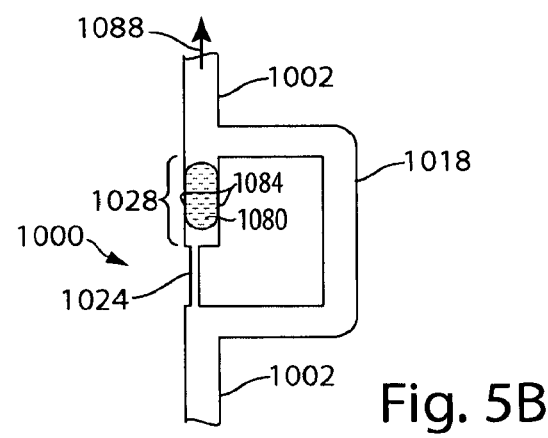
Figure 5C:
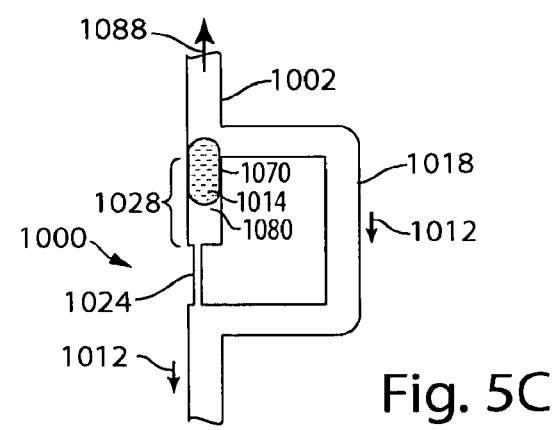

FIGS. 5A-5C show schematically the treatment of a droplet positioned at a predetermined region within a microfluidic network with a stabilizing agent according to one embodiment of the invention. As described above, droplet 1080 can be positioned at region 1028 by flowing a carrier fluid and the droplet in the direction of arrow 1012. After the droplet has been positioned, the droplet may wet a surface of the channel, such as surface portions 1084. In some embodiments, this can cause the droplet to be immobilized at this region, even when a carrier fluid is flowed in the opposite direction (e.g., in the direction of arrow 1088) in attempt to remove the droplet from this region. In such embodiments, a fluid comprising a stabilizing agent (e.g., a surfactant) can be flowed in the direction of arrow 1088 through microfluidic channel 1002. A portion of this fluid can flow through narrow path portion 1024 to reach droplet 1080 at region 1028. This fluid containing the stabilizing agent can cause the droplet to be coated with the stabilizing agent, which can result in the droplet de-wetting from the channel at surface portions 1084. In such cases, the surface tension of the droplet has been reduced. Thus, the droplet may be "depinned" from one or more surfaces of the channel. If desired, after introduction of a fluid containing a stabilizing agent to the droplet, the fluid flow may be stopped for a certain amount of time to allow the stabilizing agent to coat the droplet. In other embodiments, however, flow in channel 1002 is not stopped after the stabilizing agent has been introduced. In yet other embodiments, after a droplet has been de-wetted from a surface of the microfluidic network, fluid flowing in the microfluidic network may be replaced by a second fluid (which may or may not contain a stabilizing agent). As shown in the embodiment illustrated in FIG. 5C, droplet 1080 can be removed/extracted from region 1028 in the direction of arrow 1088. One of ordinary skill in the art can determine appropriate conditions for de-wetting a droplet from a surface of the microfluidic network which may depend on conditions such as the concentration of the stabilizing agent in the fluid, the flow rate, the degree of wetting of the droplet, the contents of the droplet, the material composition of the fluidic network, as well as other factors.

Figure 6:
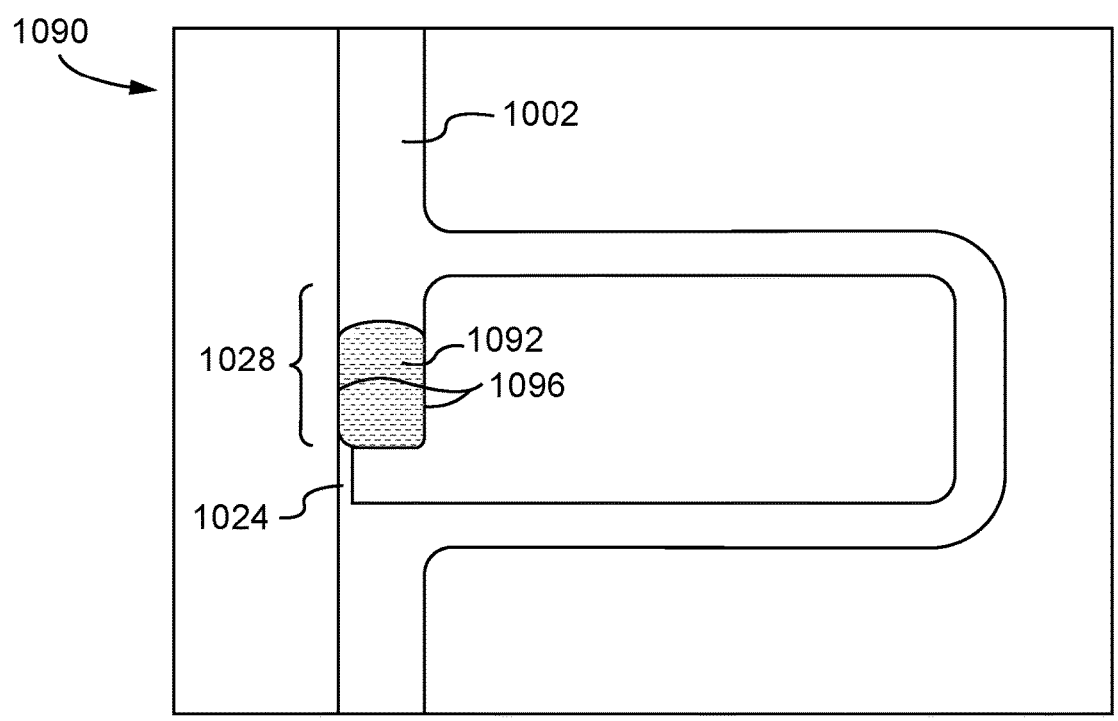
FIG. 6 is a photograph of a droplet wetting a surface of the microfluidic network according to another embodiment of the invention.
Figure 7:
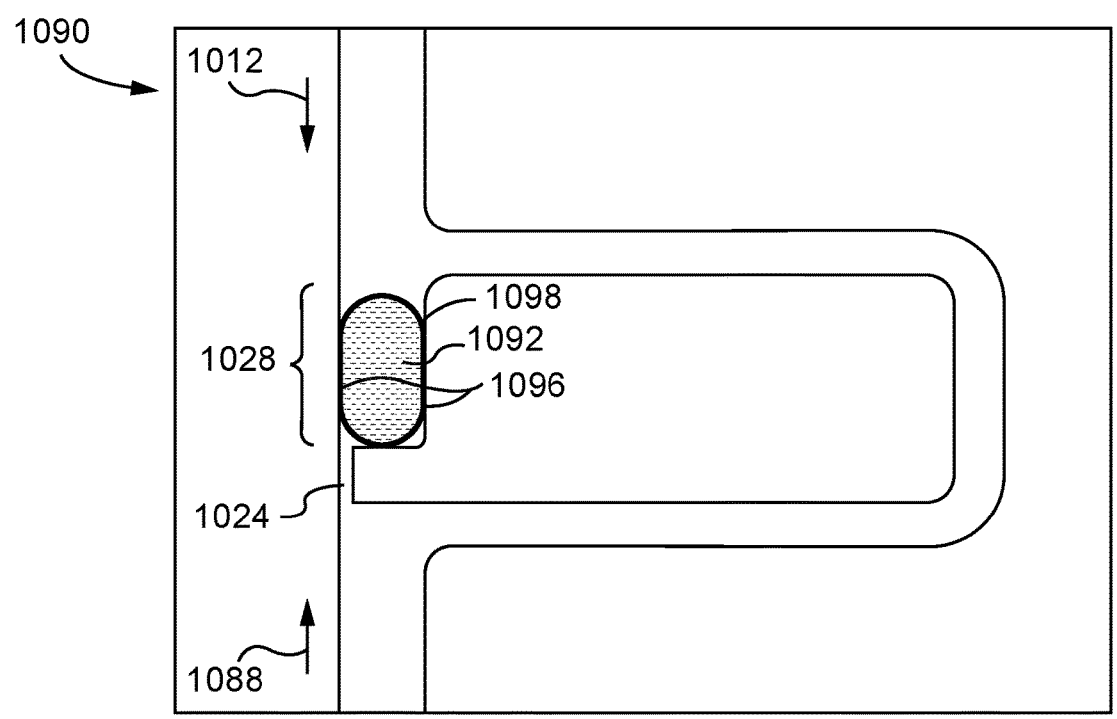
FIG. 7 shows de-wetting of the droplet from a surface of the microfluidic network after being treated with a stabilizing agent according to another embodiment of the invention.

FIG. 6 is a photograph showing droplet 1092 that has wetted surface portions 1096 of microfluidic network 1090 at region 1028. As shown in FIG. 7, after flowing a fluid containing a surfactant in the direction of arrow 1088, a portion of which flows through a narrow path portion 1024, droplet 1092 de-wets surface portions 1096 and is now stabilized with the stabilizing agent. The stabilization is evident by meniscus 1098 that forms around droplet 1092, as the droplet now takes on a lower energy state configuration compared to that shown in FIG. 6.

It should be understood that a fluid containing a stabilizing agent can be introduced into microfluidic network 1090 in any suitable manner. For example, in some embodiments, the stabilizing agent may be introduced by a fluid flowing in the direction of arrow 1012. In other embodiments, region 1028 may be in fluidic communication with another portion of the device branching from region 1028. For instance, above or below region 1028 may be a reservoir, a channel, or other component that can be used to introduce a stabilizing agent or other entity to a droplet in that region.

As shown in FIGS. 2 and 5, droplets that are released from a region of a microfluidic network can be caused to flow in a direction opposite that which was used to position the droplet in the region. In other embodiments, however, after a droplet has been removed from region in which it was positioned, the droplet may be caused to flow in the same direction as that which was used to position the droplet. For example, in one embodiment, droplet 1080 of FIG. 5C can be released from position 1028 and can be caused to flow in the direction of 1088 until the droplet resides at a downstream portion of channel 1002 (e.g., at the top of microfluidic network 1000 as shown in FIG. 5C). Then, a valve or other component that may be positioned at position 1070 can be at least partially closed to cause a higher resistance to fluid flow in fluid flow path 1014 compared to that of 1018. Since fluid flow path 1018 now has a lower resistance to fluid flow, flow of the carrier fluid can now be reversed such that it flows in the direction of arrow 1012, in which case the droplet can bypass fluid flow path 1014 and enter fluid flow path 1018.

As described above, methods for storing and/or extracting droplets in a microfluidic network are provided herein. In some embodiments, the droplets may be stored and/or extracted in sequential order. For example, the droplets may be extracted in the order they are stored or positioned in predetermined regions in the microfluidic network. Advantageously, in some embodiments, such methods do not require the use of surfactants or other stabilizing agents, since the droplets may not come into substantial physical contact with one another in a manner that causes coalescence. This is advantageous in certain cases as surfactants may interfere with contents such as proteins inside the droplet, as is known to those of ordinary skill in the art.

In some embodiments, the microfluidic networks shown in FIGS. 1-7 can be combined with one or more of the features shown in FIGS. 8-18 below. For instance, regions 1028 of FIG. 1A for positioning a droplet can replace microwells 2130 of FIGS. 8 and 14 and/or micro wells or regions in other embodiments shown in FIGS. 8-18. Thus, the microfluidic networks of FIGS. 1-7 may be a part of the microfluidic chips described in connection with FIGS. 8-18 and may be connected to any suitable component shown in these figures.

As described above, microfluidic chips described herein may include a region for forming droplets of sample in a carrier fluid (e.g., an oil), and one or more microreactor regions (also called "predetermined regions" or "regions" herein) in which the droplets can be positioned and reaction conditions within the droplet can be varied. For instance, one such system includes microreactor regions containing several (e.g., 1000) microwells or other structures that are fluidically connected to a microchannel, or formed as a part of the microchannel. A reservoir (i.e., in the form of a chamber or a channel) for containing a gas or a liquid can be situated underneath a microwell, separating the microwell by a semi-permeable barrier (e.g., a dialysis membrane). In some cases, the semi-permeable barrier enables chemical communication of certain components between the reservoir and the microwell; for instance, the semi-permeable barrier may allow water, but not proteins, to pass across it. Using the barrier, a condition in the reservoir, such as concentration or ionic strength, can be changed (e.g., by replacing the fluid in the reservoir), thus causing the indirect change in a condition of a droplet positioned inside the microwell. This format allows control and the testing of many reaction conditions simultaneously. Microfluidic chips and methods of the invention can be used in a variety of settings. One such setting, described in more detail below, involves the use of a microfluidic chip for crystallizing proteins within aqueous droplets of fluid. Advantageously, crystallization conditions can be controlled such that nucleation and growth of crystals can be decoupled, performed reversibly, and controlled independently of each other, thereby enabling the formation of defect-free crystals.

Figure 8A:
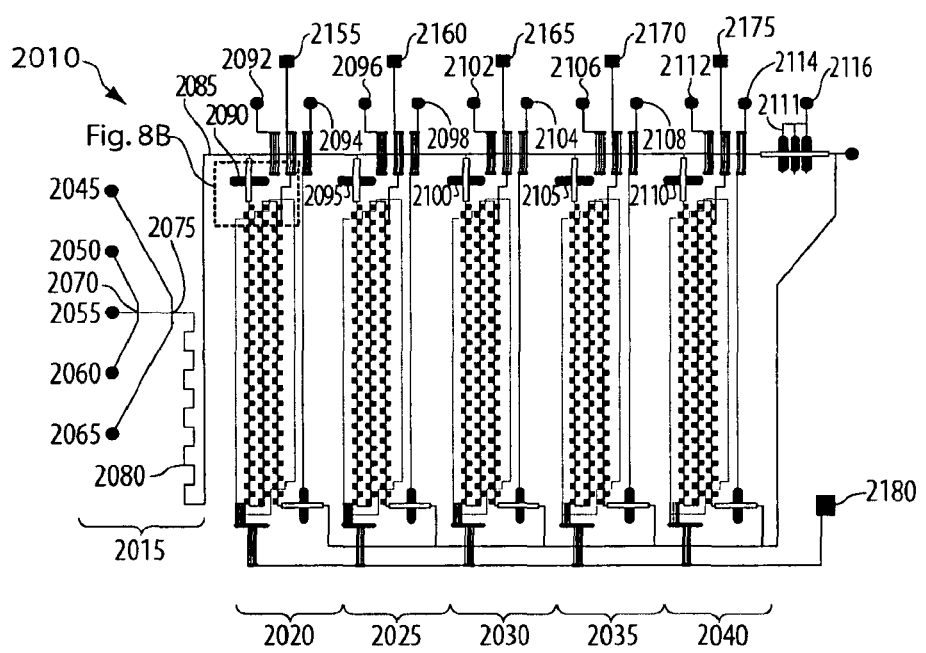
FIGS. 8A-8D show schematically a microfluidic device for manipulating fluids and reactions, according to another embodiment of the invention.
Figure 8B:
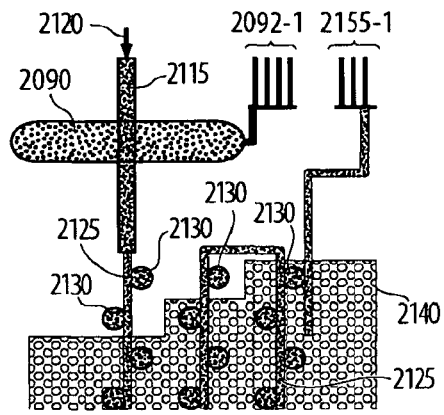
Figure 8C:
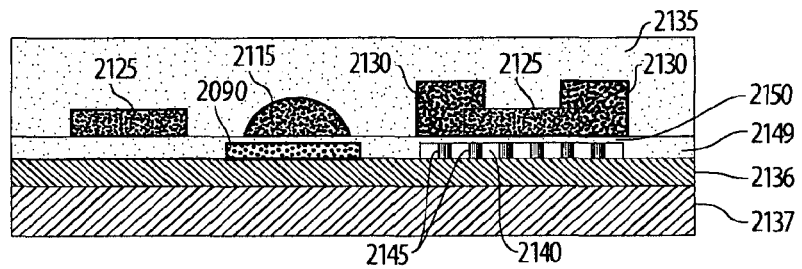

FIGS. 8A-8C illustrate a microfluidic chip 2010 according to one embodiment of the invention. As shown in FIG. 8 A, microfluidic chip 2010 contains a droplet formation region 2015 connected fluidically to several microreactor regions 2020, 2025, 2030, 2035, and 2040. The droplet formation region can include several inlets 2045, 2050, 2055, 2060, and 2065, which may be used for introducing different fluids into the chip. For instance, inlets 2050, 2055, and 2060 may each contain different aqueous solutions necessary for protein crystallization. The rate of introduction of each of the solutions into inlets 2050, 2055, and 2060 can be varied so that the chemical composition of each of the droplets is different, as discussed in more detail below. Inlets 2045 and 2065 may contain a carrier fluid, such as an oil immiscible with the fluids in inlets 2050, 2055, and 2060. Fluids in inlets 2050, 2055, and 2060 can flow (i.e., laminarly) and merge at intersection 2070. When this combined fluid reaches intersection 2075, droplets of aqueous solution can be formed in the carrier fluid. Droplet formation region 2015 also includes a mixing region 2080, where fluids within each droplet can mix, e.g., by diffusion or by the generation of chaotic flows.

Droplets formed from region 2015 can enter one, or more, of microreactor regions 2020, 2025, 2030, 2035, or 2040 via channel 2085. The particular microreactor region in which the droplets enter can be controlled by valves 2090, 2095, 2100, 2105, 2110, and/or 2111, which can be activated by valve controls 2092, 2094, 2096, 2098, 2102, 2104, 2106, 2108, 2112, 2114, and/or 2116. For example, for droplets to enter microreactor region 2020, valve 2090 can be opened by activating valve controls 2092 and 2094, while valves 2095, 2100, 2105, 2110, and 2111 are closed. This may allow the droplets to flow into channel 2115 in the direction of arrow 2120, and then into channel 2125 and to several microwells 2130 (FIGS. 8B and 8C). As discussed in more detail below, each droplet can be positioned in a microwell, i.e., by the use of surface tension forces. Any of a number of valves and/or pumps, including peristaltic valves and/or pumps, suitable for use in a fluidic network such as that described herein can be selected by those of ordinary skill in the art including, but not limited to, those described in U.S. Pat. No. 6,767,194, "Valves and Pumps for Microfluidic Systems and Methods for Making Microfluidic Systems", and U.S. Pat. No. 6,793,753, "Method of Making a Microfabricated Elastomeric Valve," which are incorporated herein by reference.

As shown in FIG. 8C, microwells 2130 (as well as channels 2115 and 2125, and other components) can be defined by voids within structure 2135, which can be made of a polymer such as poly(dimethylsiloxane) (PDMS). Structure 2135 can be supported by optional support layers 2136 and/or 2137 which can be fully or partially polymeric or made of another substance including ceramic, silicon, or other material selected for structural rigidity suitable for the intended purpose of the particular device. As illustrated in this embodiment, reservoir 2140 and posts 2145 are positioned below microwells 2130 as part of layer 2149, and separate the microwells by a semi-permeable barrier 2150. In the embodiment illustrated in FIG. 8C, semi-permeable barrier is formed in layer 2149. In some instances, semi-permeable barrier 2150 allows certain low molecular weight components (e.g., water, vapor, gases, and low molecular weight organic solvents such as dioxane and isopropanol) to pass across it, while preventing larger molecular weight components (e.g., salts, proteins, and hydrocarbon-based polymers) and/or certain fluorinated components (e.g., fluorocarbon-based polymers) from passing between microwells 2130 and reservoir 2140. By controlling the substances entering reservoir inlet 2155 (i.e., for microreactor region 2020), a condition (e.g., concentration, ionic strength, or type of fluid) in the reservoir can be changed. This can result in the change of a condition in microwells 2130 indirectly by a process such as diffusion and/or by flow of components past barrier 2150, as discussed below. Because there may be several (e.g., 1000) microwells on a chip, many reaction conditions can be tested simultaneously. Once a reaction has occurred in a droplet, the droplet can be transported, e.g., out of the device or to another portion of the device, for instance, via outlet 2180.

Figure 8D:
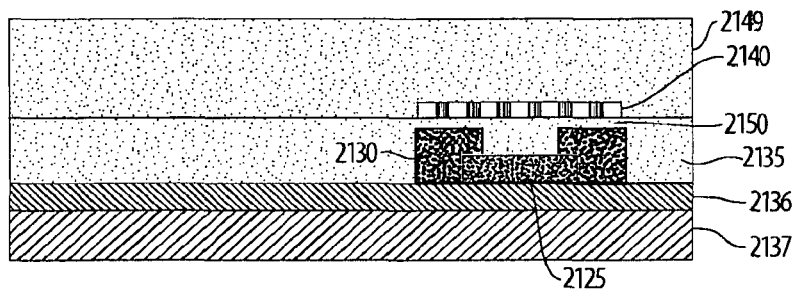

FIG. 8D shows an alternative configuration for the fabrication of device 2010. As illustrated in this figure, layer 2149 comprising reservoir 2140 is positioned above structure 2135 comprising microwells 2130 and channel 2125. In this embodiment, semi-permeable barrier 2150 is formed as part of structure 2135 i.e., by spin coating.

In the embodiment illustrated in FIG. 8D the membrane is fabricated as part of the layer containing the microwells, while as shown in FIG. 8C, the semi-permeable membrane is fabricated as part of the reservoir layer. In each case the layer containing the membrane can be thin (e.g., less than about 20 microns thick) and can be fabricated via spin coating, while the other layer(s) can be thick (e.g., greater than about 1 mm) and may be fabricated by casting a fluid. In other embodiments, however, semi-permeable barrier can be formed independently of layers 2149 and/or structure 2135, as described in more detail below.

It is to be understood that the structural arrangement illustrated in the figures and described herein is but one example, and that other structural arrangement can be selected. For example, a microfluidic network can be created by casting or spin coating a material, such as a polymer, from a mold such that the material defines a substrate having a surface into which are formed channels, and over which a layer of material is placed to define enclosed channels such as microfluidic channels. In another arrangement a material can be cast, spin-coated, or otherwise formed including a series of voids extending throughout one dimension (e.g., the thickness) of the material and additional material layers are positioned on both sides of the first material, partially or fully enclosing the voids to define channels or other fluidic network structures. The particular fabrication method and structural arrangement is not critical to many embodiments of the invention. In other cases, a particular structural arrangement or set of structural arrangements can define one or more aspects of the invention, as described herein.

Figure 9:
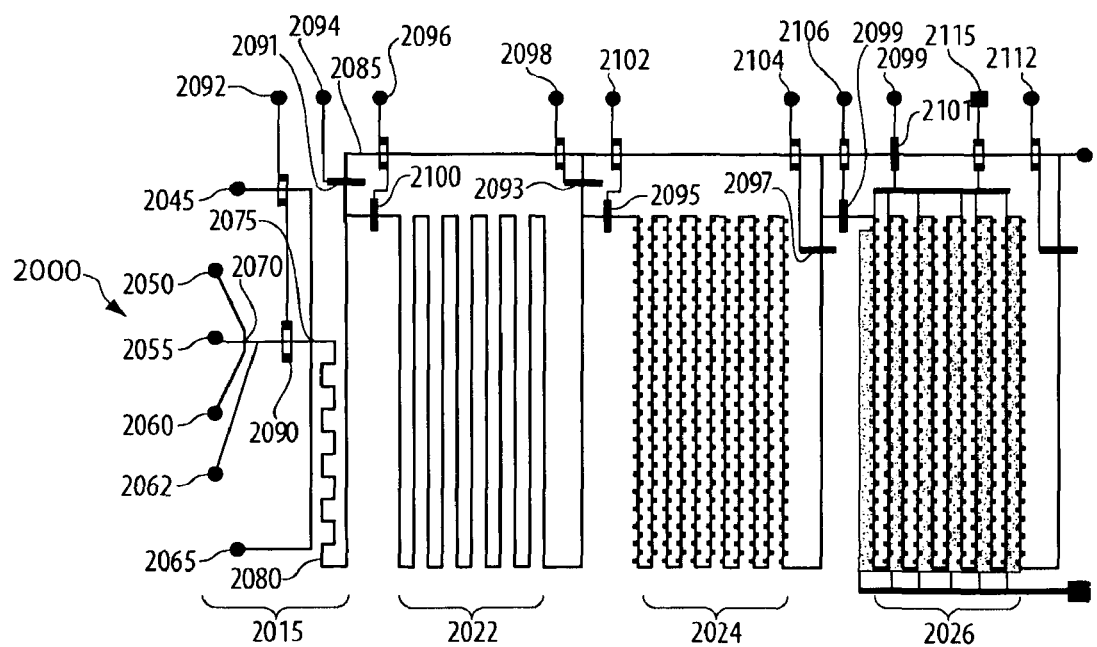
FIG. 9 shows schematically another microfluidic device for manipulating fluids and reactions, according to another embodiment of the invention.

FIG. 9 shows another exemplary design of a microfluidic chip, device 2000, which includes droplet formation region 2015, buffer region 2022, micro well region 2024, and microreactor region 2026. Buffer region 2022 can be used, for example, to allow a droplet formed in the droplet region to equilibrate with a carrier fluid. The buffer region is connected to microwell region 2024, which can be used for storing droplets. Microwell region 2024 is connected to microreactor region 2026, which contains microwells and reservoir channels positioned beneath the microwells, i.e., for changing a condition within droplets that are stored in the microwells. Droplets formed at intersection 2075 can enter regions 2022, 2024, or 2026, depending on the actuation of a series of valves. For instance, a droplet can enter buffer region 2022 by opening valve 2090 and 2100, while closing valve 2091. A droplet can enter microwell region 2024 directly by opening valves 2090, 2091, 2093, and 2095 while closing valves 2097, 2099, 2100, and 2101.

Figure 10A:
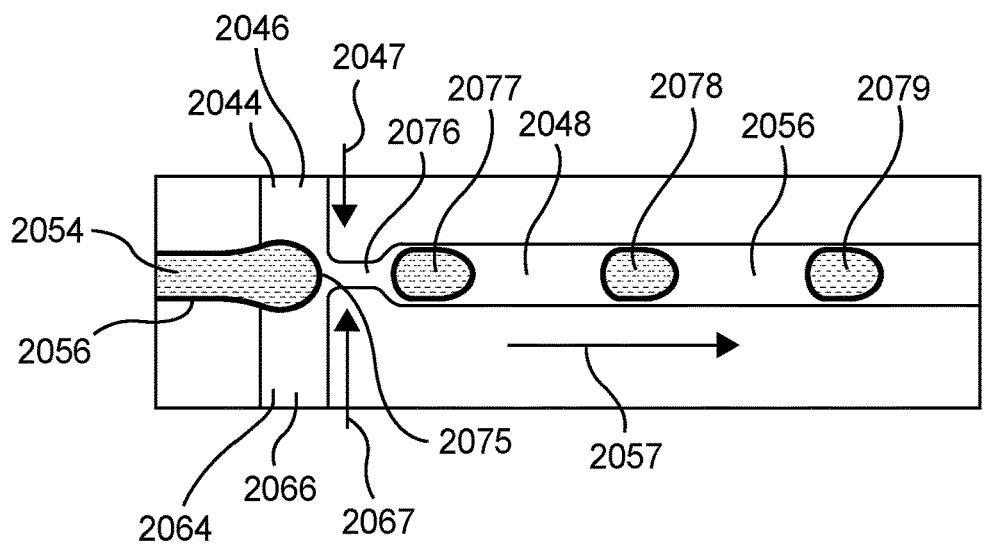
FIG. 10A is a photograph showing the formation of droplets, according to another embodiment of the invention.

The formation of droplets at intersection 2075 of device 2000 is shown in FIG. 10A. As shown in this diagram, fluid 2054 flows in channel 2056 in the direction of arrow 2057. Fluid 2054 may be, for example, an aqueous solution containing a mixture of components from inlets 2050, 2055, 2060, and 2062 (FIG. 9). Fluid 2044 flows in channel 2046 in the direction of arrow 2047, and fluid 2064 flows in channel 2066 in the direction of arrow 2067. In this particular embodiment, fluids 2044 and 2064 have the same chemical composition and serve as a carrier fluid 2048, which is immiscible with fluid 2054. In other embodiments, however, fluids 2044 and 2064 can have different chemical compositions and/or miscibilities relative to each other and to fluid 2054. At intersection 2075, droplets 2077, 2078, and 2079 are formed by hydrodynamic focusing after passing through nozzle 2076. These droplets are carried (or flowed) in channel 2056 in the direction of arrow 2057.

Droplets of varying sizes and volumes may be generated within the microfluidic system. These sizes and volumes can vary depending on factors such as fluid viscosities, infusion rates, and nozzle size/configuration. In some cases, it may be desirable for each droplet to have the same volume so that different conditions (e.g., concentrations) can be tested between different droplets, while the initial volumes of the droplets are constant. In other cases, it may be suitable to generate different volumes of droplets for use in an assay. Droplets may be chosen to have different volumes depending on the particular application. For example, droplets can have volumes of less than 1 µL, less than 0.1 µL, less than 10 nL, less than 1 nL, less than 0.1 nL, or less than 10 pL. It may be suitable to have small droplets (e.g., 10 pL or less), for instance, when testing many (e.g., 1000) droplets for different reaction conditions so that the total volume of sample consumed is low. On the other hand, large (e.g., 10 nL-1 µL) droplets may be suitable, for instance, when a reaction condition is known and the objective is to generate large amounts of product within the droplets.

The rate of droplet formation can be varied by changing the flow rates of the aqueous and/or oil solutions (or other combination of immiscible fluids defining carrier fluid and droplet, which behave similarly to oil and water, and which can be selected by those of ordinary skill in the art). Any suitable flow rate for producing droplets can be used; for example, flow rates of less than 100 nL/s, less than 10 nL/s, or less than 1 nL/s. In one embodiment, droplets having volumes between 0.1 to 1.0 nL can be formed while flow rates are set at 100 nL/s. Under these conditions, droplets can be produced at a frequency of 100 droplets/s. In another embodiment, the flow rates of two aqueous solutions can be varied, while the flow rate of the oil solution is held constant, as discussed in more detail below.

FIG. 11 shows one example of a method for positioning droplets within regions of a microfluidic channel. In the embodiment illustrated in FIG. 11A, carrier fluid 2048 flows in channel 2056 in the direction of arrow 2057 while droplets 2078 and 2079 are positioned in microwells 2082 and 2083, respectively. Droplet 2077 is carried in fluid 2048 also in the direction of arrow 2057. Droplet 2077 passes and may physically contact droplet 2079, but does not coalesce with droplet 2079 since the surfaces of the droplets may include a surfactant that prevents coalescence. As shown in FIG. 11B, when droplet 2077 is adjacent to microwell 2082, droplet 2077 tries to enter into this microwell. Since droplet 2078 has already occupied microwell 2082, however, droplet 2077 cannot fit and does not enter into this microwell. Meanwhile, the pressure of the carrier fluid pushes droplet 2077 forward in the direction of arrow 2057. When droplet 2077 passes an empty microwell, e.g., microwell 2081, droplet 2077 can enter and be positioned in this microwell (FIGS. 11D-11F). In a similar manner, the next droplet behind (i.e., to the left of) droplet 2077 can fill the next available microwell to the right of microwell 2081 (not shown). The passing of one droplet over another that has already been positioned into a microwell is referred to as the "leapfrog" method. In the leapfrog method, the most upstream microwell can contain the first droplet formed and the most downstream microwell can contain the last droplet formed.

Because droplets are carried past each other (e.g., as in FIGS. 11A-11C), and/or for other reasons involving various embodiments of the invention, a surfactant may be added to the droplet to stabilize the droplets against coalescence. Any suitable surfactant such as a detergent for stabilizing droplets can be used, including anionic, non-ionic, or cationic surfactants. In one embodiment, a suitable detergent is the non-ionic surfactant Span 80, which does not denature proteins yet stabilizes the droplets. Criteria for choosing other suitable surfactants are discussed in more detail below.

Different types of carrier fluids can be used to carry droplets in a device. Carrier fluids can be hydrophilic (i.e., aqueous) or hydrophobic (i.e., an oil), and may be chosen depending on the type of droplet being formed (i.e., aqueous or oil-based) and the type of process occurring in the droplet (i.e., crystallization or a chemical reaction). In some cases, a carrier fluid may comprise a fluorocarbon. In some embodiments, the carrier fluid is immiscible with the fluid in the droplet. In other embodiments, the carrier fluid is slightly miscible with the fluid in the droplet. Sometimes, a hydrophobic carrier fluid, which is immiscible with the aqueous fluid defining the droplet, is slightly water soluble. For example, oils such as PDMS and poly(trifluoropropylmethylsiloxane) are slightly water soluble. These carrier fluids may be suitable when fluid communication between the droplet and another fluid (i.e., a fluid in the reservoir) is desired. Diffusion of water from a droplet, through the carrier fluid, and into a reservoir containing air is one example of such a case.

A droplet can enter into an empty microwell by a variety of methods. In the embodiment shown in FIG. 11A, droplet 2077 is surrounded by an oil and is forced to flow through channel 2056, which has a large width ($W_{56}$), but small height ($h_{56}$). Because of its confinement, droplet 2077 has an elongated shape while positioned in channel 2056, as the top, bottom, and side surfaces of the droplet take on the shape of the channel. This elongated shape imparts a high surface energy on the droplet (i.e., at the oil/water interface) compared to the same droplet having a spherical shape (i.e., of the same volume). When droplet 2077 passes an empty microwell 2081, which has a larger cross-sectional dimension (e.g., height, $h_{130}$) than that of channel 2056, droplet 2077 favors the microwell since the dimensions of the microwell allow the droplet to form a more spherical shape (as shown in FIG. 11F), thereby lowering its surface energy. In other words, when droplet 2077 is adjacent to empty microwell 2081, the gradient between the height of the channel and the height in the microwell produces a gradient in the surface area of the droplet, and therefore a gradient in the interfacial energy of the droplet, which generates a force on the droplet driving it out of the confining channel and into the microwell. Using this method, droplets can be positioned serially in the next available microwell (e.g., an empty microwell) while the carrier fluid is flowing. In other embodiments, methods such as patterned surface energy, electrowetting, and dielectrophoresis can drive droplets into precise locations in microfluidic systems.

In another embodiment, a method for positioning droplets into regions (e.g., microwells) of a microfluidic network comprises flowing a plurality (e.g., at least 2, at least 10, at least 50, at least 100, at least 500, or at least 1,000) of droplets in a carrier fluid in a microfluidic channel at a first flow rate. The first flow rate may be fast, for instance, for forming many droplets quickly and/or for filling the microfluidic network quickly with many droplets. At a fast flow rate, the droplets may not position into the regions. When the carrier fluid is flowed at a second flow rate slower than the first flow rate, however, each droplet may position into a region closest to the droplet and remain in the region. This method of filling microwells is referred to as the "fast flow/slow flow" method. Using this method, the droplets can be positioned in the order that the droplets are flowed into the channel, although in some instances, not every region may be filled (i.e., a first and a second droplet that are positioned in their respective regions may be separated by an empty region). Since this method does not require droplets to pass over filled regions (e.g., microwells containing droplets), as is the case as shown in FIG. 11, the droplets may not require surfactants when this method of positioning is implemented.

Figure 12A:
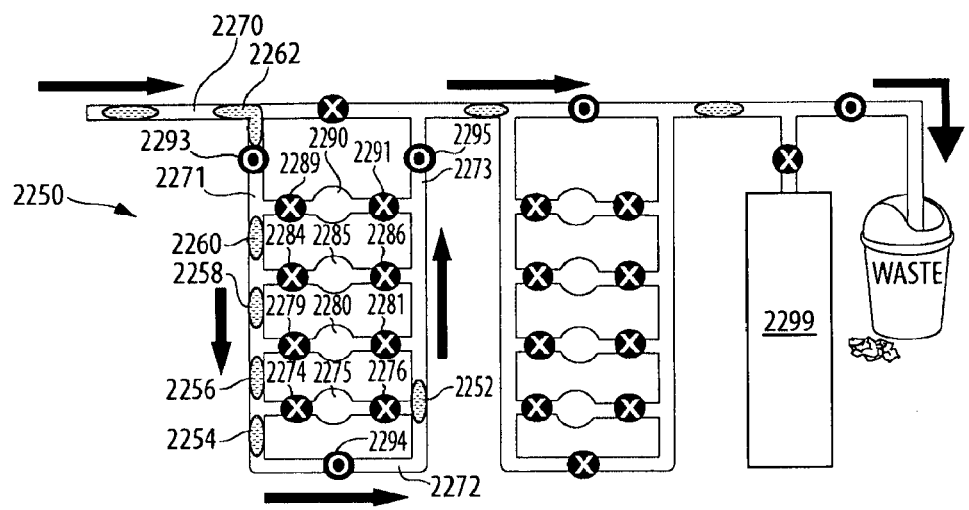
FIGS. 12A-12B show the positioning of droplets within micro wells of a microfluidic device using valves to open and close the entrance and exits of micro wells, according to another embodiment of the invention.
Figure 12B:
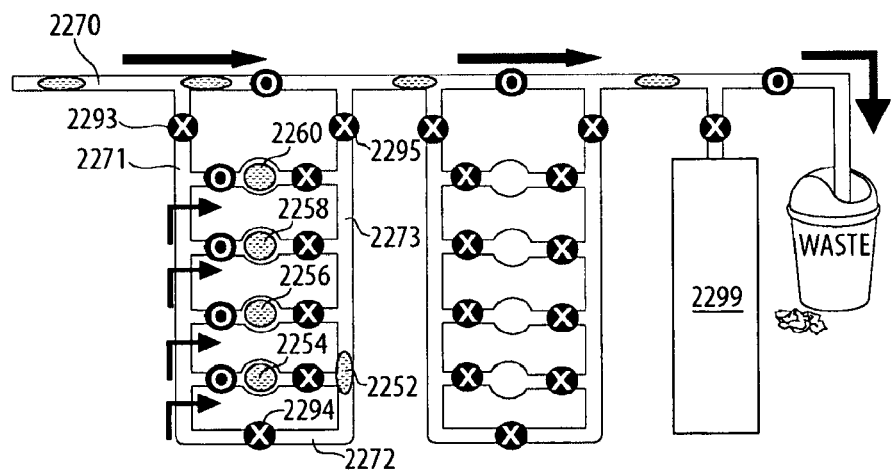

Another method for filling microwells in the order that the droplets are formed is by using valves at entrances and exits of the microwells, as shown in FIG. 12. In this illustrative embodiment, droplets 2252, 2254, 2256, 2258, 2260, and 2262 are flowed into device 2250 comprising channels 2270, 2271, 2272, and 2273, and microwells 2275, 2280, 2285, and 2290. Each microwell can have an entrance valve (e.g., valves 2274, 2279, 2284, and 2289) and an exit valve (e.g., valves 2276, 2281, 2286, and 2291) in either opened or closed positions. For illustrative purposes, opened valves are marked as "o" and closed valves are marked as "x" in FIG. 12. The droplets can flow in channels 2270, 2271, 2272, and 2273, i.e., when valves 2293, 2294, and 2295 are in the open position (FIG. 12A). Once the channels are filled, the flow in channels 2271, 2272, and 2273 can be stopped (i.e., by closing valves 2293, 2294, and 2295) and the entrance valves to the microwells can be opened (FIG. 12B). The droplets can position into the nearest microwell by surface tension or by other forces, as discussed below. If a concentration-dependent chemical process (e.g., crystallization) has occurred in a microwell, both the entrance and exit valves of that particular microwell can be opened while optionally keeping the other valves closed, and a product of the concentration-dependent chemical process (e.g., a crystal) can be flushed into vessel 2299, such as an x-ray capillary or a NMR tube, for further analysis.

Microwells may have any suitable size, volume, shape, and/or configuration, i.e., for positioning a droplet depending on the application. For example, microwells may have a cross-sectional dimension of less than about 250 µm, less than about 100 µm, or less than about 50 µm.

In some embodiments, microwells can have a volume of less than 10 µL, less than 1 µL, less than 0.1 µL, less than 10 nL, less than 1 nL, less than 0.1 nL, or less than 10 pL. Microwells may have a large volume (e.g., 0.1-10 µL) for storing large droplets, or small volumes (e.g., 10 pL or less) for storing small droplets.

In the embodiment illustrated in FIG. 11, microwells 2081, 2082, and 2083 have the same dimensions. However, in certain other embodiments, the microwells can have different dimensions relative to one another, e.g., for holding droplets of different sizes. For instance, a microfluidic chip can comprise both large and small microwells, where large droplets may favor the large microwells and small droplets may favor the small microwells. By varying the size of the microwells and/or the size of the droplets on a chip, positioning of the droplets not only depends on whether or not the microwell is empty, but also on whether or not the sizes of the microwell and the droplet match. The positioning of different droplets of different sizes may be useful for varying reaction conditions within an assay.

In another embodiment, microwells 2081, 2082, and 2083 have different shapes. For example, one microwell may be square, another may be rectangular, and another may have a pyramidal shape. Different shapes of microwells may allow droplets to have different surface energies while positioned in the microwell, and can cause a droplet to favor one shape over another. Different shapes of microwells can also be used in combination with droplets of different size, such that droplets of certain sizes favor particular shapes of microwells.

Sometimes, a droplet can be released from a microwell, e.g., after a reaction has occurred inside of a droplet. Different sizes, shapes, and/or configurations of microwells may influence the ability of a droplet to be released from the microwell.

In some cases, the size of the microwell is approximately the same size as the droplet, as shown in FIG. 11. For instance, the volume of the microwell can be less than approximately twice the volume of the droplet. This is particularly useful for positioning a single droplet within a single microwell. In other cases, however, more than one droplet can be positioned in a microwell. Having more than one droplet in a microwell can be useful for applications that require the merging of two droplets into one larger droplet, and for applications that include allowing a component to pass (e.g., diffuse) from one droplet to another adjacent droplet.

Although many embodiments illustrated herein show the positioning of droplets in microwells, in some cases, microwells are not required for positioning droplets. For instance, in some cases, a droplet is positioned in a region in fluid communication with the channel, the region having a different affinity for the droplet than does another part of the channel. The region may be positioned on a wall of the channel. In one embodiment, the region can protrude from a surface (e.g., a side) of the channel. In another embodiment, the region can have at least one dimension (e.g., a width or height) larger than a dimension of the channel. A droplet that is carried in the channel may be positioned into the region by the lowering of the surface energy of the droplet when positioned in the region, relative to the surface energy of the droplet prior to being positioned in the region.

In another embodiment, positioning of a droplet does not require the use of differences in dimension between the region and the channel. A region may have a patterned surface (e.g., a hydrophobic or hydrophilic patch, a surface patterned with a specific chemical moiety, or a magnetic patch) that favors the positioning and/or containing of a droplet. Different methods of positioning, e.g., based on hydrophobic/hydrophilic interactions, magnetic interactions, or electrical interactions such as dielectrophoresis, electrophoresis, and optical trapping, as well as chemical interactions (e.g., covalent interactions, hydrogen-bonding, van der Waals interactions, and adsorption) between the droplet and the first region are possible. In some cases, the region may be positioned in, or adjacent to, the channel, for example.

In some instances, a condition within a droplet can be controlled after the droplet has been formed. For example, FIG. 13 shows an example of a microreactor region 2026 of device 2000 (FIG. 9). The microreactor region can be used to control a condition in a droplet indirectly, e.g., by changing a condition in a reservoir adjacent to a microwell rather than by changing a condition in the microwell directly. Region 2026 includes a series of microwells used to position droplets 2201-2208, the microwells and droplets being separated from reservoir 2140 by semi-permeable barrier 2150. In this particular example, all droplets contain a saline solution and are surrounded by an immiscible oil. As shown in the figure, some droplets (droplets 2201-2204) are positioned in microwells that are farther away from the reservoir than others (droplets 2205-2208). As such, a change in a condition in reservoir 2140 has a greater immediate effect on droplets 2205-2208 than on droplets 2201-2204. Droplets 2201-2208 initially have the same volume in microreactor region 2026 (not shown).

Figures 13A, 13C:
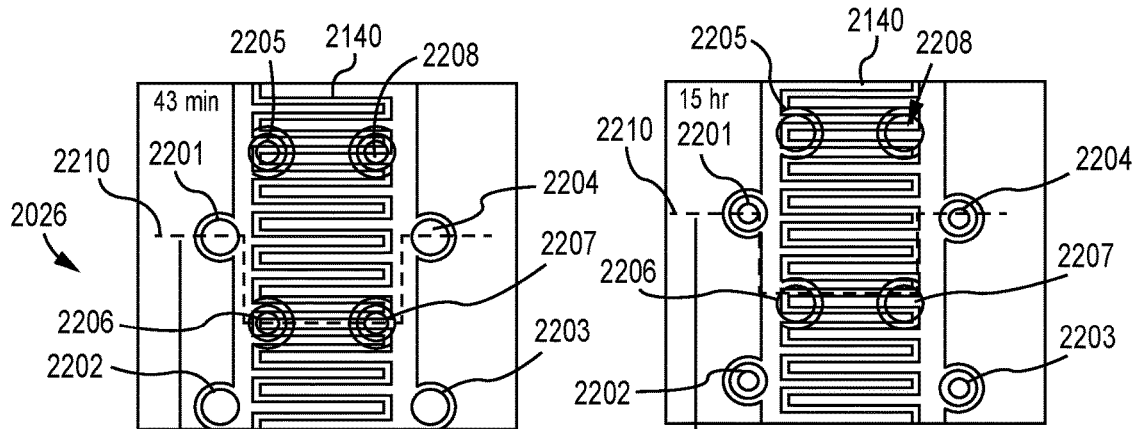
FIGS. 13A-13D show examples of changing the sizes of droplets in a microreactor region of a device, according to another embodiment of the invention.
Figure 13B:
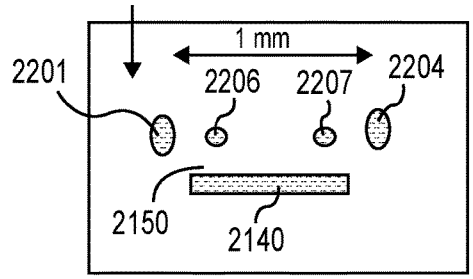
Figure 13D:
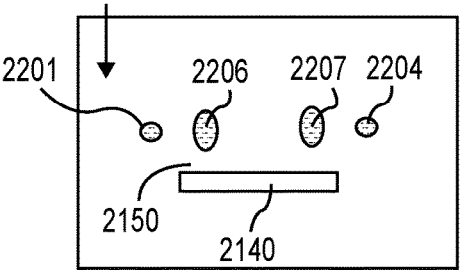

FIGS. 13A (top view) and 13B (side view of droplets 2201, 2204, 2206, 2207) show an effect that can result from circulating air in the reservoir. Air in the reservoir, in certain amounts and in connection with conditions that can be selected by those of ordinary skill in the art based upon this disclosure (e.g. amount, flow rate, temperature, etc. taken in conjunction with the makeup of the droplets) can cause droplets 2205-2208 to decrease in volume more than that of droplets 2201-2204, since droplets 2205-2208 are positioned closer to the reservoir than droplets 2201-2204. Through the process of permeation, fluids in the droplets can move across the semi-permeable barrier, causing the volume of the droplets to decrease. As shown in FIGS. 13C (top view) and 13D (side view of droplets 2201, 2204, 2206, 2207), under appropriate conditions flowing water in the reservoir instead of air reverses this process. Small droplets 2205-2208 of FIGS. 13A and 13B can swell, as illustrated in FIGS. 13C and 13D because, for instance, the droplets may contain a saline solution or otherwise have an appropriate difference in osmotic potential compared to the surrounding environment. This difference in osmotic potential can cause water to diffuse from the reservoir, across the semi-permeable barrier, through the oil, and into the droplets. Droplets farther away from the reservoir (droplets 2201-2204) may initially remain small, since it takes a longer time for water to diffuse across a longer distance (e.g., diffusion time scales with the square of the distance). At equilibrium, the chemical potentials of the fluid in the reservoir and the fluid in the droplets generally will be equal.

As shown in FIG. 13, reservoir 2140 is in the form of a microfluidic channel. In other embodiments, however, the reservoir can take on different forms, shapes, and/or configurations, so long as it can be used to store a fluid. For instance, as shown in FIG. 8C, reservoir 2140 is in the form of a chamber, and a series of microfluidic channels 2155-1 allow fluidic access to the chamber (i.e., to introduce different fluids into the reservoir). Sometimes, reservoirs can have components such as posts 2145, which may give structured support to the reservoir.

A fluidic chip can include several reservoirs that are controlled independently (or dependently) of each other. For instance, a device can include greater than 1, great than 5, greater than 10, greater than 100, greater than 1,000, or greater than 10,000 reservoirs. A large number (e.g., 100 or more) of reservoirs may be suitable for a chip in which reservoirs and microwells are paired such that a single reservoir is used to control conditions in a single microwell. A small number (e.g., 10 or less) of reservoirs may be suitable when it is favorable for many microwells to experience the same changes in conditions relative to one another. This type of system can be used, for example, for increasing the size of many droplets (i.e., diluting components within the droplets) simultaneously.

Reservoir 2140 typically has at least one cross-sectional dimension in the micron-range. For instance, the reservoir may have a length, width, or height of less than 500 µm, less than 250 µm, less than 100 µm, less than 50 µm, less than 10 µm, or less than 1 µm. The volume of the reservoir can also vary; for example, it may have a volume of less than 50 µL, less than 10 µL, less than 1 µl, less than 100 nL, less than 10 nL, less than 1 nL, less than 100 pL, or less than 10 pL. In one particular embodiment, a reservoir can have dimensions of 10 mm by 3 mm by 50 µm and a volume of less than 20 µL.

A large reservoir (e.g., a reservoir having a large cross-sectional dimension and/or a large volume) may be useful when the reservoir is used to control the conditions in several (e.g., 100) microwells, and/or for storing a large amount of fluid. A large amount of fluid in the reservoir can be useful, for example, when droplets are stored for a long time (i.e., since, in some embodiments, material from the droplet may permeate into surrounding areas or structures over time). A small reservoir (e.g., a reservoir having a small cross-sectional dimension and/or a small volume) may be suitable when a single reservoir is used to control conditions in a single microwell and/or for cases where a droplet is stored for shorter periods of time.

Semi-permeable barrier 2150 is another factor that controls the rate of equilibration or the rate of passage of a component between the reservoir and the microwells. In other words, the semi-permeable barrier controls the degree of chemical communication between two sides of the barrier. Examples of semi-permeable barriers include dialysis membranes, PDMS membranes, polycarbonate films, meshes, porous layers of packed particles, and the like. Properties of the barrier that may affect the rate of passage of a component across the barrier include: the material in which the barrier is fabricated, thickness, porosity, surface area, charge, and hydrophobicity/hydrophilicity of the barrier.

The barrier may be fabricated in any suitable material and/or in any suitable configuration in order to permit one set of components and inhibit another set of components from crossing the barrier. In one embodiment, the semi-permeable barrier comprises the material from which the reservoir is formed, i.e., as part of layer 2149 as shown in FIG. 8C, and can be formed in the same process in which the reservoir is formed (i.e., the reservoir and the barrier can be formed in a single process in which a precursor fluid is spin-coated or solution-cast onto a mold and subsequently hardened to form both the barrier and reservoir in a single step, or, alternatively, another process in which the barrier and reservoir are formed from the same material, optionally simultaneously). In another embodiment, the semi-permeable barrier comprises the same material as the structure of the device, i.e., as part of structure 2135 as shown in FIG. 8D, and can be formed in conjunction with the structure 2135 as described above in connection with the semi-permeable barrier and reservoir, optionally. For instance, all, or a portion of, the barrier can be formed in the same material as the structure layer and/or reservoir layer. In some cases, the barrier can be fabricated in a mixture of materials, one of the materials being the same material as the structure layer and/or reservoir layer. Fabricating the barrier in the same material as the structure layer and/or reservoir layer offers certain advantages such as easy integration of the barrier into the device. In other embodiments, the semi-permeable barrier is fabricated as a layer independent of the structure layer and reservoir layer. The semi-permeable barrier can be made in the same or a different material than the other layers of the device.

In some cases, the barrier is fabricated in a polymer (e.g., a siloxane, polycarbonate, cellulose, etc.) that allows passage of a first set of low molecular weight components, but inhibits the passage of a second set of large molecular weight components across the barrier. For instance, a first set of low molecular weight components may include water, gases (e.g., air, oxygen, and nitrogen), water vapor (e.g., saturated or unsaturated), and low molecular weight organic solvents (e.g., hexadecane), and the second set of large molecular weight components may include proteins, polymers, amphiphiles, and/or others species. Those of ordinary skill in the art can readily select a suitable material for the barrier based upon e.g., its porosity, its rigidity, its inertness to (i.e., freedom from degradation by) a fluid to be passed through it, and/or its robustness at a temperature at which a particular device is to be used.

The semi-permeable barrier may have any suitable thickness for allowing one set of components to pass across the barrier while inhibiting another set of components. For example, a semi-permeable barrier may have a thickness of less than 10 mm, less than 1 mm, less than 500 µm, less than 100 µm, less than 50 µm, or less than 20 µm, or less than 1 µm. A thick barrier (e.g., 10 mm) may be useful for allowing slow passage of a component between the reservoir and the microwell. A thin barrier (e.g., less than 20 µm thick) can be used when it is desirable for a component to be passed quickly across the barrier.

For size exclusive semi-permeable barriers (i.e., including dialysis membranes), the pores of the barriers can have different shapes and/or sizes. In one embodiment, the sizes of the pores of the barrier are based on the inherent properties of the barrier, such as the degree of cross-linking of the material in which the barrier is fabricated. In another embodiment, the pores of the barrier are machine-fabricated in a film of a material. Semi-permeable barriers may have pores sizes of less than 100 µm, less than 10 µm, less than 1 µm, less than 100 nm, less than 10 nm, or less than 1 nm, and may be chosen depending on the component to be excluded from crossing the barrier.

A semi-permeable barrier may exclude one or more components from passing across it by methods other than size-exclusion, for example, by methods based on charge, van der Waals interactions, hydrophilic or hydrophobic interactions, magnetic interactions, and the like. For instance, the barrier may inhibit magnetic particles but allow non-magnetic particles to pass across it (or vice versa).

Different methods of passing a component across the semi-permeable barrier can be used. For instance, in one embodiment, the component may diffuse across the barrier if there is a difference in concentration of the component between the microwell and the reservoir. In another embodiment, if the component is water, water can pass across the barrier by osmosis. In yet another embodiment, the component can evaporate across the barrier; for instance, a fluid in the microwell can evaporate across the barrier if a gas is positioned in the reservoir. In some cases, the component can cross the barrier by bulk or mass flow in response to a pressure gradient in the microwell or the reservoir. In other cases, the component can cross the barrier by methods such as facilitated diffusion or by active transport. A combination of modes of transport can also be applied. Typically, however, the barrier is not constructed and arranged to be operatively opened and closed to permit and inhibit fluid flow in the reservoir, microwell, or microchannel. For instance, in one embodiment, the barrier does not act as a valve that can operatively open and close to allow and block, respectively, fluidic access to the reservoir, microwell, or microchannel.

In some cases, the barrier is positioned in a device such that fluid can flow adjacent to a first side of the barrier without the need for the fluid to flow through the barrier. For instance, in one embodiment, a barrier is positioned between a reservoir and a microwell; the reservoir has an inlet and an outlet that allow fluidic access to it, and the microwell is fluidically connected to a microchannel having an inlet and an outlet, which allow fluidic access to the microwell. Fluid can flow in the reservoir without necessarily passing across the barrier (i.e., into the microchannel and/or microwell), and the same or a different fluid can flow in the microchannel and/or microwell without necessarily passing across the barrier (i.e., into the reservoir).

FIG. 14 shows that device 2010 can be used to grow, and control the growth of, a precipitate such as crystal inside a microwell of the device. In this particular embodiment, droplet 2079 is aqueous and contains a mixture of components, e.g., a protein, a salt, and a buffer solution, for generating a crystal. The components are introduced into the device via inlets 2050, 2055, and/or 2060. An immiscible oil introduced into inlets 2045 and 2065 serves as carrier fluid 2048. As shown schematically in FIG. 14B, droplet 2079 is surrounded by carrier fluid 2048 in microwell 2130. Semi-permeable barrier 2150 separates the microwell from reservoir 2140, which can contain posts 2145.

Protein in droplet 2079 can be nucleated to form crystal 2300 by concentrating the protein solution within the droplet (FIG. 14C). If the protein solution is concentrated to a certain degree, the solution becomes supersaturated and suitable for crystal growth. In one embodiment, the protein solution is concentrated by flowing air in reservoir 2150, which causes water in the droplet to evaporate across the semi-permeable barrier while the protein remains in the droplet. In another embodiment, a high ionic strength buffer (i.e., a buffer having higher ionic strength than the ionic strength of the fluid defining the droplet) is flowed in the reservoir. The imbalance of chemical potential between the two solutions causes water to diffuse from the droplet to reservoir. Other methods for concentrating the solution within the droplet can also be used.

Other methods for nucleating a crystal can also be applied. For instance, two droplets, each of which contain a component necessary for protein crystallization, can be positioned in a single microwell. The two droplets can be fused together into a single droplet, i.e., by changing the concentration of surfactant in the droplets, thereby causing the components of the two droplets to mix. In some cases, these conditions may be suffice to cause nucleation.

As shown in FIGS. 14C and 14D, once crystal 2300 is nucleated in a droplet, the crystal grows spontaneously within a short period of time (e.g., 10 seconds) since the crystal is surrounded by a supersaturated solution (as discussed in more detail below). In some cases, this rapid growth of the crystal leads to poor-quality crystals, since defects do not have time to anneal out of the crystal. One solution to this problem is to change the conditions of the sample during the crystallization process. Ideal crystal growing conditions occur when the sample is temporarily brought into deep supersaturation where the nucleation rate is high enough to be tolerable. In the ideal scenario, after a crystal has nucleated, the supersaturation of the solution would be decreased, e.g., by lowering the protein or salt concentrations or by raising temperature, in order to suppress further crystal nucleation and to establish conditions where slow, defect free crystal growth occurs. Device 2010 can allow this process to occur by decreasing the size of a crystal after it has nucleated and grown, and then re-growing the crystal slowly under moderately supersaturated conditions. Thus, the processes of nucleation and growth can be performed reversibly, and can occur independently of each other, in embodiments such as device 2010.

To decrease the size of the crystal (i.e., so that the crystal can be re-grown to become defect-free), reservoir 2140 can be filled with a buffer of lower salt concentration than that of the protein solution in the droplet. This causes water to flow in the opposite direction, i.e., from the reservoir to the protein solution, which dilutes the protein and the precipitant (e.g., by increasing the volume of the droplet), suppresses further nucleation, and slows down growth (FIG. 14E). To re-grow the crystal under slower and more moderately supersaturated conditions, the fluid in the reservoir can be replaced by a solution having a higher salt concentration such that fluid diffuses slowly out of the droplet, thereby causing the protein in the droplet to concentrate.

If the dialysis step of decreasing the size of the crystal proceeds long enough that the crystal dissolves completely, this system (e.g., device 2010) can advantageously allow the processes of nucleation and growth to be reversed, i.e., by changing the fluids in the reservoir. In addition, if small volumes of the droplets (e.g., ~nL) are used in this system, the device allows faster equilibration times between the droplet and the reservoir than for microliter-sized droplets, which are used in conventional vapor diffusion-based crystallization techniques (e.g., hanging or sitting drop techniques).

In some cases, concentrating the protein solution within the droplet causes the nucleation of precipitate (FIG. 14F). The precipitate may comprise largely noncrystalline material, largely crystalline material, or a combination of both non-crystalline and crystalline material, depending on the growth conditions applied. Device 2010 can be used to dilute the protein solution in the droplet, which can cause some, or all, of the precipitate to dissolve. Sometimes, the precipitate is dissolved until a small portion of the precipitate remains. For instance, dissolving may cause the smaller portions of the precipitate to dissolve, allowing one or a few of the largest portions to remain; these remaining portions can be used as seeds for growing crystals. After a seed has been formed, the concentration of protein in the droplet can be increased slowly (e.g., by allowing water to diffuse slowly out of the droplet). This process can allow the formation of large crystals within the droplet (FIG. 14G).

As shown in FIGS. 14A-14G, processes such as nucleation, growth, and dissolution of a crystal can all occur within a droplet while the droplet is positioned in the same microwell. In other embodiments, however, different processes can occur in different parts or regions of the fluidic network. For instance, nucleation and dissolution of a crystal can take place in a small (e.g., 10 pL) droplet in a small microwell, and then the droplet containing the crystal can be transported to a larger microwell for re-growth of the crystal in a larger (e.g., 1 nL) droplet. This process may allow small amounts of reagent to be consumed for the testing of reaction conditions and larger amounts of reagent to be used when reaction conditions are known. In some cases, this process decreases the overall amount of reagent consumed, as discussed in more detail below.

Device 2010 of FIG. 15 can be used to form many droplets of different composition, and to precisely control the rate and duration of supersaturation of the protein solution within each droplet. The rate of introduction of protein, salt, and buffer solutions into inlets 2050, 2055, and 2060 can be varied so that the solutions can be combinatorially mixed with each other to produce several (e.g., 1000) droplets having different chemical compositions. In one embodiment, each droplet has the same volume (e.g., 2 nL), and each droplet can contain, for instance, 1 nL of protein solution and 1 nL of the other solutes. The rate of introducing the protein solution can be held constant, while the rates of introducing the salt and buffer solutions can vary. For example, injection of the salt solution can ramp up linearly in time (e.g., from 0 to 10 nL/s), while injection of the buffer solution ramps down linearly in time (e.g., from 10 to 0 nL/s). In another embodiment, the rate of introducing a protein can vary while one of the other solutes is held constant. In yet another embodiment, all solutions introduced into the device can be varied, i.e., in order to make droplets of varying sizes. Advantageously, this setup can allow many different conditions for protein crystallization to be tested simultaneously.

Figure 15A:
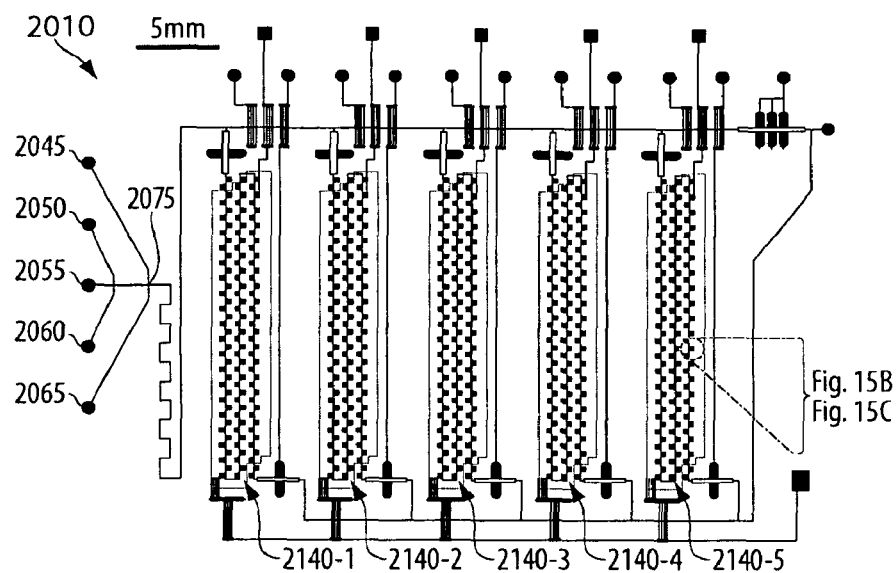
FIGS. 15A-15C show the increase and decrease of the size of a crystal inside a micro well of a device, according to another embodiment of the invention.
Figure 15B:
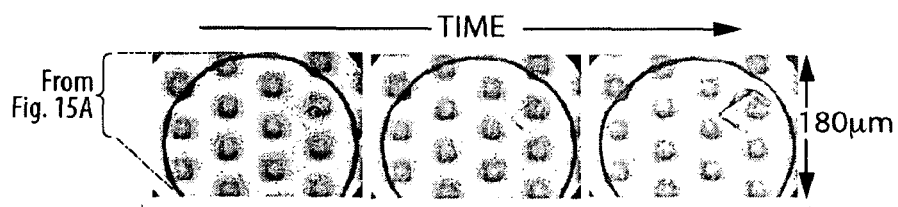

In addition to varying the concentration of solutes within each droplet, the environmental factors influencing crystallization can be changed. For instance, device 2010 includes five independent reservoirs 2140-1, 2140-2, 2140-3, 2140-4, and 2140-5 that can contain solutions of different chemical potential. These reservoirs can be used to vary the degree of supersaturation of the protein solution within the droplets. Thus, the nucleation rate of the first crystal produced and the growth rate of the crystal can be controlled precisely within each droplet. Examples of controlling the sizes of crystals are shown in FIGS. 15B and 15 C, and in Example 3.

Figure 16A:
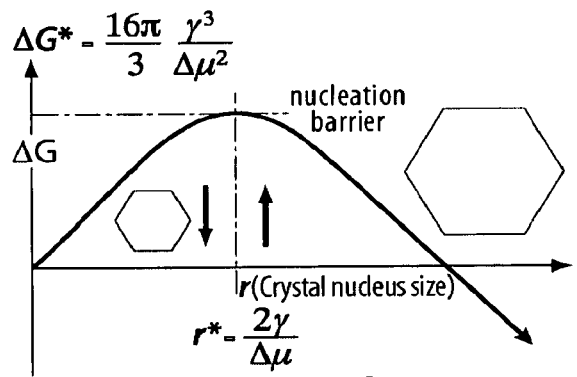
FIG. 16A is a plot showing the relationship between free energy and crystal nucleus size, according to another embodiment of the invention.
Figure 16B:
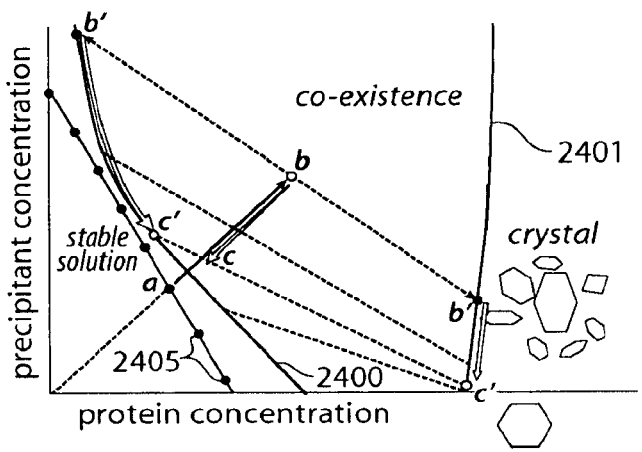
FIG. 16B is a phase diagram showing the relationship between precipitation concentration and protein concentration, according to another embodiment of the invention.

FIG. 16B is a phase diagram illustrating the use of a reservoir to change a condition in a droplet (i.e., by reversible dialysis). At low protein concentrations, a protein solution is thermodynamically stable (i.e., in the stable solution phase). An increase in concentration of a precipitant, such as salt or poly(ethylene) glycol (PEG), drives the protein into a region of the phase diagram where the solution is metastable and protein crystals are stable (i.e., in the co-existence phase). In this region, there is a free energy barrier to nucleating protein crystals and the nucleation rate can be extremely slow (FIG. 16A). At higher concentrations, the nucleation barrier is suppressed and homogeneous nucleation occurs rapidly (i.e., in the crystal phase). As mentioned above, at high supersaturation, crystal growth is rapid and defects may not have time to anneal out of the crystal, leading to poor quality crystals. Thus, production of protein crystals requires two conditions that work against each other. On one hand, high supersaturation is needed for nucleating crystals, but on the other hand, low supersaturation is necessary for crystal growth to proceed slowly enough for defects to anneal away. Changing sample conditions during the crystallization process is one method for solving this problem. Ideal crystal growing conditions occur when the sample is temporarily brought into deep supersaturation where the nucleation rate is high enough to be tolerable. In the ideal scenario, after a few crystals have nucleated, the supersaturation of the solution would be decreased by either lowering the protein or salt concentrations, or by raising temperature in order to suppress further crystal nucleation and to establish conditions where slow, defect free crystal growth occurs. In other words, independent control of nucleation and growth is desired.

Figure 17:
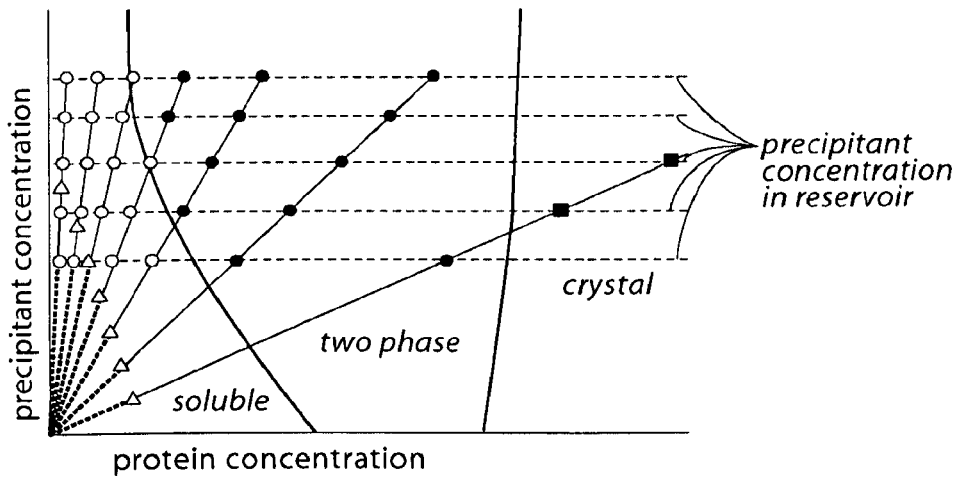
FIG. 17 is another phase diagram showing the relationship between precipitation concentration and protein concentration, according to another embodiment of the invention.

As shown in FIG. 16B, a microfluidic device (e.g., device 2010) of the present invention can be used to independently control nucleation and growth of a crystal. In FIG. 16B, lines 2400 and 2401 separate the liquid-crystal phase boundary. Dashed tie-lines connect co-existing concentrations, with crystals high in protein and low in precipitant (e.g., polyethylene glycol (PEG)). For clarity, the composition trajectory for one initial condition is shown here, while FIG. 17 shows trajectories for multiple initial and final conditions. Reversible microdialysis can be shown in three steps. Step 1: Initial concentrations of solutions in the droplets are stable solutions (circles 2405—points a). Step 2: Dialysis against high salt or air (e.g., in the reservoir) removes water from the droplet, concentrating the protein and precipitant within the droplet (path a→b). At point b, the solution is metastable and if crystals nucleate, then phase separation occurs along tie-lines (b→b'), producing small crystals that grow rapidly. Step 3: Dialysis against low salt water dilutes the protein and precipitant within the droplets, which lowers $\Delta\mu$ and increases $\Delta G^*$ and $r^*$. This suppresses further nucleation, causes the small crystals to dissolve adiabatically along the equilibrium phase boundary (b'→c'), and slows the growth of the remaining large crystals. If there was no nucleation at point b, then the metastable solution would evolve from b→c. Step 4: If necessary, crystalline defects can be annealed away by alternately growing and shrinking individual crystals b'↔c' which is accomplished by appropriately varying the reservoir conditions.

The size of a crystal that has been formed in a droplet can vary (i.e., using device 2010 of FIG. 15). For example, a crystal may have a linear dimension of less than 500 µm, less than 250 µm, less than 100 µm, less than 50 µm, less than 25 µm, less than 10 µm, or less than 1 µm. Some of these crystals can be used for X-ray diffraction and for structure determination. For instance, consider the crystals formed in 1 nL droplets. If the concentration of the protein solution introduced into the device is 10 mg/mL=10 µg/µL, then 1 µL of protein solution only contains 10 µg of protein. In the device, 1 µL of protein solution can produce 1,000 droplets of different composition, for example, each droplet containing 1 nL of protein solution and 1 nL of other solutes, as described above. The linear dimension of a 1 nL drop is 100 µm and if the crystal is 50% protein, then the crystal will have a volume 50 times smaller than the protein solution, or 20 pL. The linear dimension of a cubic crystal of 20 pL volume is roughly 25 µm, and X-ray diffraction and structure determination from such small crystals is possible.

In another embodiment, a device having two sections can be used to form crystals. The first section can be used to screen for crystallization conditions, for instance, using very small droplet volumes (e.g., 50 pL), which may be too small for producing protein crystals for X-ray diffraction and for structure determination. Once favorable conditions have been screened and identified, the protein stock solution can be diverted to a second section designed to make droplets of larger size (e.g., 1 nL) for producing crystals suitable for diffraction. Using such a device, screening, e.g., 1000 conditions at 50 pL per screen, consumes only 0.5 µg of protein. Scaling up a subset of 50 conditions to 1 nL (e.g., the most favorable conditions for crystallization) consumes another 0.5 µg of protein. Thus, it can be possible to screen 1000 conditions for protein crystallization using a total of 1 µg of protein.

In some cases, it is desirable to remove the proteins formed within the microwells of the device, for instance, to load them into vessels such as x-ray capillaries for performing x-ray diffraction, as shown in FIG. 12. In one embodiment, a microfluidic device comprises microwells that are connected to an exhaust channel and a valve that controls the passage of components from the microwell to the exhaust channel. Using the multiplexed valves, it is possible to control n valves with 2 $\log_2$ n pressure lines used to operate the valves. Droplets can first be loaded into individual microwells using surface tension forces as describe above. Then, individual microwells can be addressed in arbitrary order (e.g., as in a random access memory (RAM) device) and crystals can be delivered into x-ray capillaries. Many (e.g., 100) crystals, each isolated from the next by a plug of immiscible fluid (e.g., water-insoluble oil), can be loaded into a single capillary for diffraction analysis.

As the number of crystallization trials grows, it may be advantageous to automate the detection of crystals. In one embodiment, commercial image processing programs that are interfaced to optical microscopes equipped with stepping motor stages are employed. This software can identify and score "hits" (e.g., droplets and conditions favorable for protein crystallization). This subset of all the crystallization trials can be scanned and select crystals can be transferred to the x-ray capillary.

In another embodiment, a microfluidic device has a temperature control unit. Such a device may be fabricated in PDMS bonded to glass, or to indium tin oxide (ITO) coated glass, i.e., to improve thermal conductivity. Two thermoelectric devices can be mounted on opposite sides of the glass to create a temperature gradient. Thermoelectric devices can supply enough heat to warm or cool a microfluidic device at rates of several degrees per minute over a large temperature range. Alternatively, thermoelectric devices can maintain a stable gradient across the device. For example, device 2010 shown in FIG. 15A can have a thermoelectric device set at 40° C. on the left end (i.e., near reservoir 2140-1) and at 4° C. on the right end (i.e., near reservoir 2140-5). This arrangement can enable each of the reservoirs in between the left and right ends to reside at different temperatures. Temperature can be used as a thermodynamic variable, in analogy to concentration in FIG. 16B, to help decouple nucleation and growth.

In some cases, surfactants are required to prevent coalescence of droplets. For instance, in one embodiment, several droplets can be positioned adjacent to each other in a channel without the use of microwells, i.e., the droplets can line themselves in different arrangements along the length of the channel. In this embodiment, as well as embodiments that involve the passing of droplets beside other droplets (FIG. 11), a surfactant is required to stabilize the droplets. For each type of oil (i.e., used as a carrier fluid), there exists an optimal surfactant (i.e., an optimum oil/surfactant pair). For example, for a device that is fabricated in PDMS, the ideal pair includes a surfactant that stabilizes an aqueous droplet and does not denature the protein, and an oil that is both insoluble in PDMS, and has a water solubility similar to PDMS. Hydrocarbon-based oils such as hexadecane and dichloromethane can be poor choices, since these solvents swell and distort the PDMS device after several hours. The best candidates may be fluorocarbons and fluorosurfactants to stabilize the aqueous solution because of the low solubility of both PDMS and proteins in fluorinated compounds. The use of a hydrocarbon surfactant to stabilize protein droplets could interfere with membrane protein crystallization of protein-detergent complexes, although it is also possible that surfactants used in the protein-detergent complex also stabilizes the oil/water droplets. In one embodiment, hexadecane is used to create aqueous droplets with a gentle non-ionic detergent (e.g., Span-80) to stabilize the droplets. After the droplets are stored in the microwells, the hexadecane and Span-80 can be flushed out and replaced with fluorocarbon or paraffin oil. This process can allow the hexadecane to reside in the PDMS for a few minutes, which is too short of a time to damage the PDMS device.

In another embodiment, the droplet-stabilizing surfactant can be eliminated by having a device in which there are no microwells, and where the protein droplets are separated in a microchannel by plugs of an oil. For a device that is fabricated in a polymer such as PDMS, an oil separating the protein droplets may dissolve into the bulk of the polymer device over time. This can cause the droplets to coalesce because the droplets are not stabilized by a surfactant. In some cases (e.g., if an oil that is insoluble in the polymer cannot be found and/or if coalescence of droplets is not desired), the microfluidic structure containing the protein channels can be made from glass, and the barriers and valves can be made in a polymer (e.g., PDMS). Because the volume of the barrier is less than the volume of oil, only a small fraction of the oil can dissolve into the barrier, causing the aqueous droplets to remain isolated.

The device described above (i.e., without microwells, and where the protein droplets are separated in a microchannel by plugs of oil) may be used to control the nucleation and growth of crystals similar to that of device 2010. For instance, a semi-permeable barrier can separate the microchannel from a reservoir, and fluids such as air, vapor, water, and saline can be flowed in the reservoir to induce diffusion of water across the barrier. Therefore, swelling and shrinking of the droplet, and the formation and growth of crystals within the droplet, can be controlled.

FIG. 18 shows another example of a device that can be used to enable a concentration-dependent chemical process (e.g., crystallization) to occur. Device 2500 includes a microwell 2130 fluidically connected to microchannel 2125. Beneath the microwell are reservoirs 2140 and 2141 (e.g., in the form of microchannels, which may be connected or independent), separated by semi-permeable barrier 2150. Droplet 2079 (e.g., an aqueous droplet) may be positioned in the microwell, surrounded by an immiscible fluid (e.g., an oil), as shown in FIG. 18C. In some cases, dialysis processes similar to ones described above can be implemented. For example, fluids can be transported across the semi-permeable barrier by various methods (e.g., diffusion or evaporation) to change the concentration and/or volume of the fluid in the droplet.

In other cases, a vapor diffusion process can occur in device 2500. For instance, a portion of the oil that is used as a carrier fluid in microchannel 2125 can be blown out of the channel with a fluid such as a gas (e.g., dry air or water saturated air) by flowing the gas into an inlet of the channel. This process can be performed while the droplet remains in the microwell (FIG. 18D). Depending on the chemical potential of the gas in the channel, the droplets containing protein can concentrate or dilute. For example, if air is flowed into microchannel 2125, water from the droplet can exchange (e.g., by evaporation) out of the droplet and into the air stream. This causes the droplet to shrink in volume (FIG. 18E). To dilute the protein in the droplet and/or to increase the volume of the droplet, a stream of saturated water vapor can be flowed into microchannel 2125 (FIG. 18F).

In another embodiment, concentration-dependent chemical processes can occur in a device without the use of droplets. For instance, a first fluid can be positioned in a region of the fluidic network (e.g., in a microwell) and a second fluid can be positioned in a reservoir, the region and the reservoir separated by a semi-permeable barrier. The introduction of different fluids into the reservoir can cause a change in the concentration of components within the first region, i.e., by diffusion of certain components across the semi-permeable barrier.

To overcome the "'world to chip' interface problem" of introducing a protein solution into a microfluidic device without wasting portions of the protein solution, e.g., in connections or during the initial purging of air from the microfluidic device, devices of the present invention can be fabricated with an on-chip injection-loop system. For example, buffer region 2022 of FIG. 9 with its neighboring valves (e.g., valves 2093 and 2100) can function as an injection-loop if it is located upstream from the nozzle (i.e., upstream of intersection 2075). A volume (e.g., 1 µL) of protein solution can first be dead-end loaded into a long channel (e.g., having dimensions 100 mm×0.1 mm×0.1 mm) and then isolated with valves. Next, the device can be primed and purged of air. Once droplets are being produced steadily, the injection-loop can be connected fluidically to the flow upstream from the nozzle by the actuation of valves.

In some embodiments, regions of a fluidic network such as microchannels and micro wells are defined by voids in the structure. A structure can be fabricated of any material suitable for forming a fluidic network. Non-limiting examples of materials include polymers (e.g., polystyrene, polycarbonate, PDMS), glass, and silicon. Those of ordinary skill in the art can readily select a suitable material based upon e.g., its rigidity, its inertness to (i.e., freedom from degradation by) a fluid to be passed through it, its robustness at a temperature at which a particular device is to be used, its hydrophobicity/hydrophilicity, and/or its transparency/opacity to light (i.e., in the ultraviolet and visible regions).

In some instances, a device is comprised of a combination of two or more materials, such as the ones listed above. For instance, the channels of the device may be formed in a first material (e.g., PDMS), and a substrate can be formed in a second material (e.g., glass). In one particular example as shown in FIG. 8, structure 2135, which contains voids in the form of channels and microwells, can be made in PDMS, support layer 2136 can be made in PDMS, and support layer 2137 may be formed in glass.

Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channels of the device may be hydrophilic or hydrophobic in order to minimize the surface free energy at the interface between a material that flows within the channel and the walls of the channel. For instance, if the formation of aqueous droplets in an oil is desired, the walls of the channel can be made hydrophobic. If the formation of oil droplets in an aqueous fluid is desired, the walls of the channels can be made hydrophilic.

In some cases, the device is fabricated using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist (MicroChem), to produce a negative master of the photoresist on a silicon wafer. A positive replica of PDMS may be made by molding the PDMS against the master, a technique known to those skilled in the art. To complete the fluidic network, a flat substrate, e.g., a glass slide, silicon wafer, or a polystyrene surface, may be placed against the PDMS surface and plasma bonded together, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

In order to optimize a device of the present invention, it may be helpful to quantify the diffusion constant and solubility of certain fluids through the semipermeable barrier, if these quantities are not already known. For instance, if the barrier is fabricated in PDMS, the flux of water through the barrier can be quantified by measuring transport rates of water as a function of barrier thickness. Micro fluidic devices can be built to have a well-defined planar geometries for which analytical solutions to the diffusion equation are easily calculated. For example, a microfluidic device can be fabricated having a 2 mm by 2 mm square barrier separating a water-filled chamber from a chamber through which dry air flows. The flux can be measured by placing colloids in the water and measuring the velocity of the colloids as a function of time. Analysis of the transient and steady-state flux allows determination of the diffusion constant and solubility of water in PDMS. Similar devices can be used to measure the solubility of oil in PDMS. In order to optimize the reversible dialysis process, the flux of water into and out of the protein solutions in the droplets can be determined (e.g., as a function of droplet volume, ionic strength of the fluids in the reservoir and/or droplet, type of carrier oil, and/or thickness of the barrier) using video optical microscopy by measuring the volume of the droplets as a function of time after changing the solution in the reservoir.

The present invention is not limited by the types of proteins that can be crystallized. Examples of types of proteins include bacterially-expressed recombinant membrane channel proteins, G protein-coupled receptors heterologously expressed in a mammalian cell culture systems, membrane-bound ATPase, and membrane proteins.

Microfluidic methods have been used to screen conditions for protein crystallization, but until now this method has been applied mainly to easily handled water-soluble proteins. A current challenge in structural biology is the crystallization and structure determination of integral membrane proteins. These are water-insoluble proteins that reside in the cell membrane and control the flows of molecules into and out of the cell. They are primary molecular players in such central biological phenomena as the generation of electrical impulses in the nervous system, "cell signaling," i.e., the ability of cells to sense and respond to changes in environment, and the maintenance of organismal homeostasis parameters such as water and electrolyte balance, blood pressure, and cytoplasmic ATP levels. Despite their vast importance in maintaining cell function and viability, membrane proteins (which make up roughly 30% of proteins coded in the human genome) are under-represented in the structural database (which contains >$10^4$ water-soluble proteins and <$10^2$ membrane proteins). The reason for this scarcity is because it has been difficult to express membrane proteins in quantities large enough to permit crystallization trials, and even when such quantities are available, crystallization itself is not straight-forward.

Devices of the present invention may be used to exploit recent advances in membrane protein expression and crystallization strategies. For instance, some expression systems for prokaryotic homologues of neurobiologically important eukaryotic membrane proteins have been developed, and in a few cases these have been crystallized and structures determined by x-ray crystallography. In these cases, however, the rate-limiting step, is not the production of milligram-quantities of protein, but the screening of crystallization conditions. Membrane proteins must be crystallized from detergent solutions, and the choice and concentration of detergent have been found to be crucial additional parameters in finding conditions to form well-diffracting crystals. For this reason, a typical initial screen for a membrane protein requires systematic variation of 100-200 conditions. Sparse-matrix screens simply don't work because they are too sparse. Moreover, two additional constraints make the crystallization of membrane proteins more demanding than that of water-soluble proteins. First, the amounts of protein obtained in a typical membrane protein preparation, even in the best of cases, are much smaller than what is typically encountered in conventional water-soluble proteins (i.e., 1-10 mg rather than 50-500 mg). Second, membrane proteins are usually unstable in detergent and must be used in crystallization trials within hours of purification; they cannot be accumulated and stored. These constraints run directly against the requirement for large, systematic crystal screens.

Devices of the present invention may be used to overcome the constraints mentioned above for crystallizing membrane proteins. For example, device 2010, which can be used to perform reversible dialysis, may overcome the three limitations of membrane protein crystallization: the small amount of protein available, the short time available to handle the pure protein, and the very large number of conditions that must be tested to find suitable initial conditions for crystallization.

One of the challenges of crystallography is for the growth of extremely ordered and in some cases, large, crystals. Ordered and large crystals are suitable for ultra-high resolution data and for neutron diffraction data, respectively. These two methods are expected to provide the locations of protons, arguably the most important ions in enzymology, which are not accessible by conventional crystallography. So far, these applications have relied on serendipitous crystal formation rather than on controlled formation of crystals. Routine access of such ordered and/or large would make structural enzymology and its applications, e.g., drug design, more powerful than it is today. Certain embodiments of the current invention, with their ability to reversibly vary supersaturation, can be used to grow single crystals to large sizes, and the diffraction quality of these crystals can be characterized.

Although devices and methods of the present invention have been mainly described for crystallization, devices and methods of the invention may also be used for other types of concentration-dependent chemical processes. Non-limiting examples of such processes include chemical reactions, enzymatic reactions, immuno-based reactions (e.g., antigen-antibody), and cell-based reactions.

The following examples are intended to illustrate certain embodiments of the present invention, but are not to be construed as limiting and do not exemplify the full scope of the invention.

EXAMPLE 1

This example illustrates a procedure for fabricating a microfluidic structure used in certain embodiments of the invention. In one embodiment, a microfluidic structure comprising a series of microfluidic channels and microwells was made by applying a standard molding article against an appropriate master. For example, microchannels were made in PDMS by casting PDMS prepolymer (Sylgard 184, Dow Corning) onto a patterned photoresist surface relief (a master) generated by photolithography. The pattern of photoresist comprised the channels and microwells having the desired dimensions. After curing for 2 h at 65° C. in an oven, the polymer was removed from the master to give a free-standing PDMS mold with microchannels and microwells embossed on its surface. Inlets and/or outlets were cut out through the thickness of the PDMS slab using a modified borer.

A semi-permeable membrane (15 microns thick) formed in PDMS and comprising a reservoir and valve, as illustrated in FIG. 8C, was fabricated via spin coating PDMS prepolymer onto a master generated by photolithography. The master comprised a pattern of photoresist comprising the reservoir and valve having the desired dimensions. The membrane layer was cured for 1 h at 65° C. in an oven.

Next, the PDMS mold and PDMS membrane layer were sealed together by placing both pieces in a plasma oxidation chamber and oxidizing them for 1 minute. The PDMS mold was then placed onto the membrane layer with the surface relief in contact with the membrane layer. An irreversible seal formed as a result of the formation of bridging siloxane bonds (Si—O—Si) between the two substrates, caused by a condensation reaction between silanol (SiOH) groups that are present at both surfaces after plasma oxidation. After sealing, the membrane layer (with the attached PDMS mold) was removed from the master. The resulting structure was then placed against a support layer of PDMS. This example illustrates that a microfluidic structure comprising microchannels, microwells, reservoirs, and valves can be fabricated using simple lithographic procedures according to one embodiment of the invention.

EXAMPLE 2

Figure 10B:
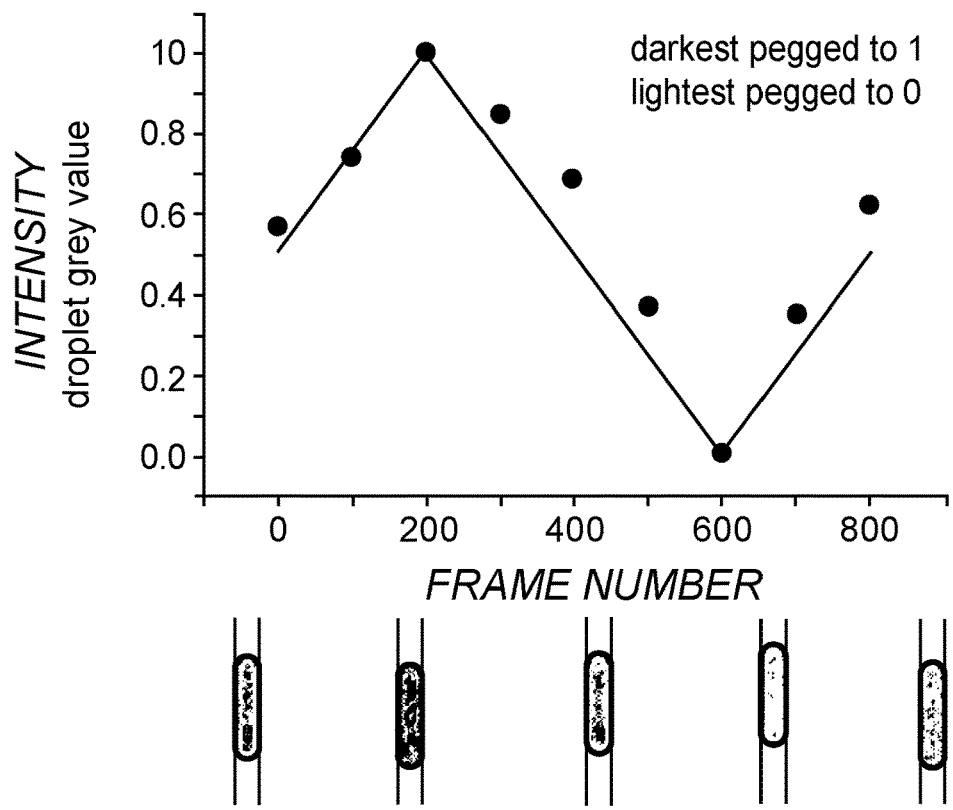
FIG. 10B shows a plot illustrating the combinatorial mixing of solutes in different droplets, according to another embodiment of the invention.

FIG. 10B shows the use of colloids to test combinatorial mixing of solutes and to visualize fluid flow using a microfluidic structure as generally illustrated in FIG. 9, which was made by the procedures generally described in Example 1. The colloid particles, 1 μm in size with a size variation of 2.3%, were made by Interfacial Dynamic Corporation. The concentration of the colloids was about 1%. The colloid suspension and buffer solution were flowed into inlets 2050 and 2060, respectively, using syringes connected to a syringe pump made by Harvard Apparatus, PHD2000 Programmable. The colloids were mixed with buffer by linearly varying the flow rates of the colloid suspension and buffer solution; for instance, the flow rate of the colloidal suspension was linearly and repeatedly varied from 80 μl/hr to 20 μl/hr while the flow rate of the buffer solution was linearly and repeatedly varied from 20 μl/hr to 80 μl/hr. This was performed so that the total flow rate of the aqueous suspension was kept constant at 100 μl/hr, and so that the drop size remained constant. The transmitted light intensity through the droplets was proportional to the colloid concentration. The transmitted light intensity was measured by estimating the gray scale of droplets shown in pictures taken by a high speed camera, Phantom V5. The pictures were taken at a rate of 10,000 frames per second. The gray scale estimation was performed using Image-J software. This experiment shows that combinatorial mixing of solutes can be used to generate many (e.g., 1000) different reaction conditions, each droplet being unique to a particular condition.

EXAMPLE 3

This example shows the control of droplet size within microwells of a device. Experiments were performed using a microfluidic structure as generally illustrated in FIG. 13, which was made according to the procedures generally described in Example 1. AU microwells were 200 μm wide and 30 μm in height, and the initial diameter of the droplets while the droplets were stored in the microwells was about 200 μm. Aqueous droplets comprised a 1M, NaCl solution. The droplets flowed in a moving carrier phase of PFD (perfluorodecalin, 97%, Sigma-Aldrich). All fluids were injected into device 2026 using syringe pumps (Harvard Apparatus, PHD2000 Programmable).

Device 2026 of FIG. 13 contained two sets of microwells for holding aqueous droplets. One set of microwells contained droplets of protein solution (droplets 2205-2208) that were separated from the reservoir by a 15 μm thick PDMS membrane that was permeable to water, but not to salt, PEG, or protein. Droplets in these microwells changed their volumes rapidly in contrast to droplets in microwells that were located 100 μm away from the reservoir (e.g., droplets 2201-2204). In FIG. 13, the process of fluid exchange between the reservoir and the microwells was diffusive, and diffusion time scales with the square of the distance. Thus, the time to diffuse 100 μm was 44 times longer than the time to diffuse 15 μm.

Initially, all the droplets in FIG. 13 A were of the same size and volume. Dry air was circulated in the reservoir channel under a pressure of 15 psi, which caused the initially large droplets sitting above the reservoir to shrink substantially (i.e., droplets 2205-2208), while droplets stored in the outer wells (droplets 2201-2204) shrunk much less.

As shown in FIG. 13 C, pure water was circulated in the reservoir channel under 15 psi pressure, which caused the initially small droplets to swell (i.e., droplets 2205-2208) because the droplets contained saline solution. In this fashion, all solute concentrations of the stored droplets was reversibly varied. The outer pair of droplets stored farther away from the reservoir channels (droplets 2201-2204) changed size much slower than the droplets stored directly above the reservoir channels (droplets 2205-2208) and approximated the initial droplet conditions.

Although water does dissolve slightly into the bulk of the PDMS microfluidic device and into the carrier oil, this experiment demonstrates that diffusion through the thin PDMS membrane is the dominant mechanism governing drop size, and not solubilization of the droplets in the carrier oil or in the bulk of the PDMS device.

EXAMPLE 4

FIG. 14 shows use of the microfluidic structure generally illustrated in FIG. 8 to perform reversible microdialysis, particularly, for the crystallization and dissolving of the protein xylanase. The microfluidic structure was made according to the procedures generally described in Example 1. Solutions of xylanase (4.5 mg/mL, Hampton Research), NaCl (0.5 M, Sigma-Aldrich), and buffer (Na/K phosphate 0.17 M, pH 7) were introduced into inlets 2050, 2055, and 2060 and were combined as aqueous co-flows. Oil was introduced into inlets 2045 and 2065. All fluids were introduced into the device using syringe pumps (Harvard Apparatus, PHD2000 Programmable). Droplets of the combined solution were formed when the solution and the oil passed through a nozzle located at intersection 2075. One hundred identical droplets, each having a volume of 2 nL, were stored in microwells of device 2010.

Device 2010 comprised two layers. The upper layer comprised flow channels and microwells which contained the droplets of protein. The lower layer comprised five independent dialysis reservoirs and valves that controlled flow in the protein-containing channels of the upper layer. The two layers were separated by a 15 μm thick semi-permeable barrier 2150 made in PDMS. Square posts 2145 of PDMS covered 25% of the reservoir support the barrier. FIG. 15B is a photograph of device 2010 showing microwells 2130 and square posts 2145 that supported barrier 2150.

Figure 15C:

Crystallization occurred when dry air was introduced into the reservoir (i.e., at a pressure of 15 psi), which caused water to flow from the protein solution across the barrier and into the reservoir. Once nucleated, the crystals grew to their final size in under 10 seconds. Over 90% of the wells were observed to contain crystals. Next, air in the reservoir was replaced with distilled water (i.e., pressurized at 15 psi). Diffusion of water into the droplet caused the volume of mother liquor surrounding the crystals to increase immediately (FIG. 15C). After 15 minutes, the crystals began to dissolve rapidly and disappeared in another minute. These experiments demonstrate the feasibility of using a microfluidic device of the present invention to crystallize proteins using nanoliter volumes of sample, and the ability of these devices to perform reversible dialysis.

EXAMPLE 5

FIG. 16A is a diagram showing the energy required for nucleating a crystal. Specifically, FIG. 16A relates free energy of a spherical crystal nucleus ($\Delta G$) to the size of the crystal nucleus (r). Nucleation is an activated process because a crystal of small size costs energy to form due to the liquid–crystal surface energy ($\gamma$). The free energy of a spherical crystal nucleus of radius r is $\Delta G = \gamma 4\pi r^2 - \Delta\mu 4\pi r^3/3$. The height of the nucleation barrier ($\Delta G^*$) and critical nucleus ($r^*$) decrease as the chemical potential difference ($\Delta\mu$) between the crystal and liquid phases increases. A highly supersaturated solution (i.e., large $\Delta\mu$) will have a high nucleation rate, $\Gamma \sim \exp(-\Delta G^*/kT)$ and crystals, once nucleated, will grow rapidly.

EXAMPLE 6

The following example is a prophetic example. FIG. 17 is a schematic diagram of a typical protein phase diagram showing the relationship between precipitation concentration and protein concentration in a droplet. Experiments will be performed in the device of FIG. 15. Initially, sets of droplets in wells over each of the five reservoirs (e.g., reservoirs 2140-1, 2140-2, 2140-3, 2140-4, and 2140-5 of FIG. 15A) will contain protein solutions of different compositions (triangles). The reservoirs' precipitant concentrations are indicated as horizontal dashed lines. Each protein solution (triangles) can equilibrate with its associated reservoir through the exchange of water between the reservoir and protein solutions. The state of the five sets of protein solutions after equilibration are shown as follows: Solutions remain soluble (open circles); solutions enter two-phase region (filled circles) and phase separate into crystals; and entire solution becomes crystalline (squares). This experiment will demonstrate that entire phase diagrams can be obtained using a single microfluidic device of the present invention.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of and " consisting essentially of shall be closed or semi-closed transitional phrases, respectively, as set forth in the United States Patent Office Manual of Patent Examining Procedures, Section 2111.03.

What is claimed is:

1. A method of coalescing droplets, the method comprising:

providing a microfluidic device comprising a substrate having a plurality of separate regions positioned substantially parallel to one another and a microfluidic channel in fluid communication with the plurality of separate regions, wherein each of the plurality of separate regions comprises an inlet, an outlet, and a microwell therebetween;

flowing an oil in the microfluidic channel;

flowing a plurality of first aqueous droplets in the microfluidic channel;

positioning at least one of the plurality of first aqueous droplets into a first one of the plurality of separate regions;

flowing a plurality of second aqueous droplets in the microfluidic channel;

positioning at least one of the plurality of second aqueous droplets into the first one of the plurality of separate regions; and coalescing the at least one of the plurality of second aqueous droplets with the at least one of the plurality of first aqueous droplets to form a coalesced aqueous droplet.

2. The method of claim 1, wherein each microwell comprises a constricted fluidic path that exits the microwell.

3. The method of claim 1, wherein the oil does not comprise a surfactant.

4. The method of claim 1, wherein positioning at least one first aqueous droplet is independent of a flow rate of the oil in the microfluidic channel.

5. The method of claim 1, further comprising positioning each of the plurality of first aqueous droplets into a separate respective one of the plurality of separate regions.

6. The method of claim 1, wherein the oil comprises a surfactant.

7. The method of claim 1, wherein the microfluidic device comprises five or more separate regions.

8. The method of claim 1, wherein the coalesced aqueous droplet is in the first one of the plurality of separate regions.

9. The method of claim 1, further comprising removing the coalesced aqueous droplet from the first one of the plurality of separate regions.

* * * * *